(12) United States Patent
Bessede

(10) Patent No.: US 10,697,985 B2
(45) Date of Patent: Jun. 30, 2020

(54) METHOD FOR DETECTING SMALL MOLECULES IN A SAMPLE

(71) Applicant: IMMUSMOL SAS, Pessac (FR)

(72) Inventor: Alban Bessede, Bordeaux (FR)

(73) Assignee: IMMUSMOL SAS, Bordeaux (FR)

( * ) Notice: Subject to any disclaimer, the term of this patent is extended or adjusted under 35 U.S.C. 154(b) by 0 days.

(21) Appl. No.: 14/900,196

(22) PCT Filed: Jun. 23, 2014

(86) PCT No.: PCT/EP2014/063178
§ 371 (c)(1),
(2) Date: Mar. 4, 2016

(87) PCT Pub. No.: WO2014/202791
PCT Pub. Date: Dec. 24, 2014

(65) Prior Publication Data
US 2016/0356799 A1  Dec. 8, 2016

(30) Foreign Application Priority Data

Jun. 21, 2013 (WO) ................. PCT/EP2013/063070
Dec. 19, 2013 (GB) ................................... 1322538.8

(51) Int. Cl.
*G01N 33/94* (2006.01)
*G01N 33/577* (2006.01)

(52) U.S. Cl.
CPC .......... *G01N 33/94* (2013.01); *G01N 33/577* (2013.01)

(58) Field of Classification Search
CPC ............................. G01N 33/94; G01N 33/577
See application file for complete search history.

(56) References Cited

U.S. PATENT DOCUMENTS

| 5,656,447 | A * | 8/1997 | Namboodiri | C07K 16/18 435/7.1 |
| 7,632,928 | B2 * | 12/2009 | Law | C07K 16/44 530/403 |
| 9,234,047 | B2 * | 1/2016 | Kellermann | C07K 16/44 |
| 2015/0175712 | A1 | 6/2015 | Bessede | |

FOREIGN PATENT DOCUMENTS

| EP | 1 820 795 A1 | 8/2007 |
| EP | 2 374 802 A1 | 10/2011 |
| WO | 95/03815 A1 | 2/1995 |
| WO | 99/01125 A1 | 1/1999 |
| WO | 99/58968 A1 | 11/1999 |
| WO | 93/040102 A1 | 5/2003 |
| WO | 93/047571 A2 | 6/2003 |
| WO | 2007/024735 A2 | 3/2007 |
| WO | 2008/022281 A1 | 2/2008 |
| WO | 2008/114275 A2 | 9/2008 |
| WO | 2011/057200 A1 | 5/2011 |
| WO | 2011/062628 A1 | 5/2011 |

OTHER PUBLICATIONS

Chen et al., Kynurenine pathway metabolites in humans: disease and healthy States. Int J Tryptophan Res. 2009;2:1-19. Epub Jan. 8, 2009.
Chen et al., Recent advances in the treatment of amyotrophic lateral sclerosis. Emphasis on kynurenine pathway nhibitors. Cent Nerv Syst Agents Med Chem. Mar. 2009;9(1):32-9.
Costantino, G., New promises for manipulation of kynurenine pathway in cancer and neurological diseases. Expert Opin Ther Targets. Feb. 2009;13(2):247-58. doi: 10.1517/14728220802665734.
European Office Action for Application No. 13734364.6, dated Dec. 8, 2015 (8 pages).
Heyes, M.P. et al., "Quinolinic acid in tumors, hemorrhage and bacterial infections of the central nervous system in children," J Neural Sci. Nov. 1995;133(1-2):112-8.
International Search Report and Written Opinion for Application No. PCT/EP2013/063070, dated Oct. 25, 2013 (12 pages).
International Preliminary Report on Patentability for Application No. PCT/EP2013/063070, dated Dec. 31, 2014 (8 pages).
International Search Report and Written Opinion for Application No. PCT/EP2014/063178, dated Oct. 23, 2014 (7 pages).
International Preliminary Report on Patentability for Application No. PCT/EP2013/063178, dated Dec. 22, 2015 (5 pages).
Johnson et al., "The clinical impact of screening and other experimental tumor studies," Cancer Treatment Reviews, 1975, v. 2, pp. 1-31.
Nakano et al., Identification of novel kynurenine production-inhibiting benzenesulfonamide derivatives in cancer cells. Biochem Biophys Res Commun. Mar. 16, 2012;419(3):556-61. doi: 10.1016/j.bbrc.2012.02.059. Epub Feb. 17, 2012.
United Kingdom Search Report for Application No. GB1211120.9 dated Oct. 22, 2012 (5 pages).
Yoshikawa et al., Serum concentration of L-kynurenine predicts the clinical outcome of patients with diffuse large B-cell lymphoma treated with R-CHOP. Eur J Haematol. Apr. 2010;84(4):304-9. doi: 10.1111/j.1600-0609.2009.01393.x. Epub Nov. 7, 2009.
U.S. Appl. No. 14/409,330, filed Dec. 18, 2014, Antagonist to an Enzyme and/or a Metabolite of the Kynurenine Pathway.

* cited by examiner

*Primary Examiner* — Shafiqul Haq
(74) *Attorney, Agent, or Firm* — Meunier Carlin & Curfman LLC

(57) ABSTRACT

The present invention telates to a method for detecting small molecular analytes in a sample, which method comprises derivatizing at least one small molecular analyte or at least one carrier molecule, in such way that one can bind to the other, thus forming at least one analyte-carrier complex, adding a detection immunoligand that s binds to the analyte-carrier complex, and detecting the small molecular analyte.

12 Claims, 12 Drawing Sheets

C Cell culture supernatants

D Human urine

E Mice sera

A  Antibody characteristics

B  Kynurenic acid quantification

A  Antibody characteristics

B  Xanthurenic acid quantification

A Antibody characteristics

B Cinnabarinic acid quantification

A  Antibody characteristics

B  Quinolinic acid quantification

METHOD FOR DETECTING SMALL MOLECULES IN A SAMPLE

Figure 1:
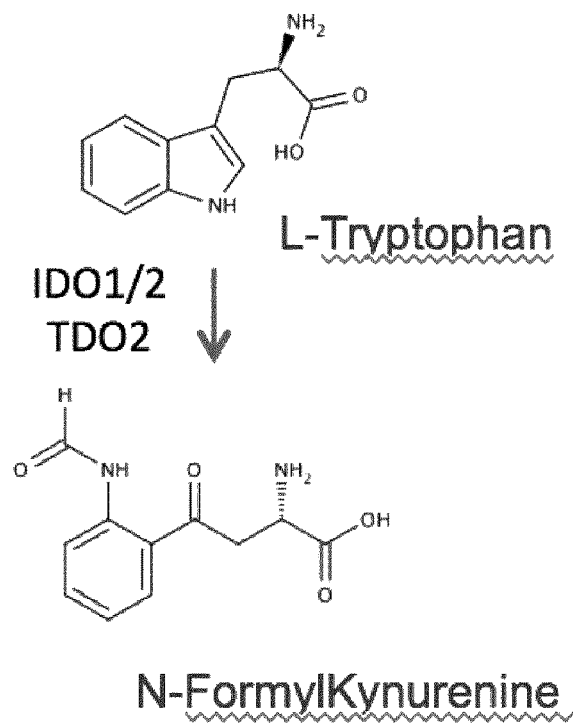

Biomedicinical research has in the past enhanced the capabilities to detect analytes in patient samples, scientific samples, forensic samples and the like. In order to detect protein-based analytes, the method preferred today is ELISA (Enzyme-linked immunosorbent assay). This is a test that uses antibodies and color change to identify a substance. Usually an antigen, in a liquid sample or wet sample.

Analytes from the sample are attached to a surface. Then, a specific antibody is applied over the surface so it can bind to the analyte. This antibody is linked to an enzyme, and, in the final step, a substance containing the enzyme's substrate is added. The subsequent reaction produces a detectable signal, most commonly a color change in the substrate.

ELISA provides superior results in terms of sensitivity and specificity, as well as robustness and reproducibility, and is thus extremely popular in analytic and scientific laboratories.

However, because of the fact that ELISA uses antibodies, only analytes can be detected that antibodies can detect. This requires that the respective analyte is immunogenic, in a way that an antibody can be made against it.

While, due to their comparatively big size, most protein analytes (like cytokines, pathogen antigens, enzymes, antibodies) are immunogenic enough for this purpose, and can thus readily be detected with ELISA, many small molecular analytes are not immunogenic because they are orders of magnitudes smaller than protein reagents. For this reason, most conventional ELISA methods cannot be used to detect small molecular analytes.

However, small molecular analytes have recently entered into the focus of scientific interest, particularly with respect to diagnostics and disease prediction and prognosis for example in cancer, neurodegenerative diseases and autoimmune diseases. Today, in most of the cases, these analytes can only be analyzed with non-ELISA methods. Suitable methods encompass mass spectrometry (MS), gas chromatography (GC) and High Performance liquid Chromatography (HPLC).

While these methods are also satisfyingly robust and sensitive, their use requires a high degree of integration and infrastructure, and the respective apparatus are more expensive. This undermines their application in point of care locations, in particular in areas of mediocre infrastructure. In contrast thereto, ELISA methods, which are less demanding, can be applied even in remote locations where external support is poor and where sophisticated infrastructure does not exist.

It would further facilitate lab person's life if they could use the same equipment for the detection of both protein analytes and small molecular analytes. This would make lab protocols much easier, speed up the respective processes, reduce overall costs and help to avoid mistakes and confusion.

SUMMARY OF THE INVENTION

It is an object of the present invention to provide a methodology that allows the detection of small molecular analytes in a sample and is an alternative to established methods.

It is another object of the present invention to provide a methodology that allows the detection of small molecular analytes in a sample and avoids disadvantages from the prior art.

It is another object of the present invention to provide a methodology that allows the detection of small molecular analytes in a sample and has less demands with respect to the degree of infrastructure, can be performed on comparatively cheap apparatus, an can be performed on the same equipment as what is used for the detection of protein analytes.

It is another object of the present invention to make such methodology accessible for forensic, scientific, epidemiologic, environmental, predictive, diagnostic or prognostic purposes.

EMBODIMENTS OF THE INVENTION

These objects are met with methods and means according to the independent claims of the present invention. The dependent claims are related to preferred embodiments. It is yet to be understood that value ranges delimited by numerical values are to be understood to include the said delimiting values.

SUMMARY OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

According to the invention a method for detecting small molecular analytes in a sample is provided, which method comprises the following steps:

a) derivatizing at least one small molecular analyte or at least one carrier molecule, in such way that one can bind to the other, thus forming at least one analyte-carrier complex, b) adding a detection immunoligand that binds to the analyte-carrier complex, and c) detecting the small molecular analyte.

The term "small molecular analyte", as used herein, relates to molecules the upper molecular weight limit for which is often set at 1000 Daltons. These analytes can for example be metabolites, i.e., educts, intermediates and products of metabolism which have various functions in an organism, including fuel, structure, signaling, stimulatory and inhibitory effects on enzymes, catalytic activity of their own (usually as a cofactor to an enzyme), defense, and interactions with other organisms (e.g. pigments, odorants, and pheromones, as well as secondary metabolite, which are not directly involved in metabolism, but usually have important functions, e.g., antibiotics and pigments such as resins and terpenes etc. Accordingly, "small molecular analytes" are preferably non-protein-like target molecules.

Such analytes have a particularly low immunogenicity, and are even more difficult to detect by antibodies when free floating. The above considerations thus apply in particular to analytes having a molecular weight of <1000 Da, preferably <500 Da, more preferably <300 Da. It is particularly surprising that the method according to the invention allows the detection of such analytes without the use of conventional methods like GC, MS or HPLC.

In a preferred embodiment of the invention, the immunoligand is at least one selected from the group consisting of
- a polyclonal or monoclonal antibody, or fragment or derivative thereof,
- a new antibody format
- a fusion peptide, and/or
- an antibody mimetic.

In another preferred embodiment of the invention, the method is an immunoassay method. An immunoassay is a biochemical test that measures the presence or concentration of a molecule in a solution through the use of an immunoligand, e.g., an antibody. The molecule to be detected by the immunoassay is often referred to as an "analyte".

In another preferred embodiment of the invention, the immunoligand is labelled. Such label may consist, e.g., of a radioisotope, an enzyme, a luminescent entity, a fluorescent entity, a phosphorescent entity, a metal-containing particle (e.g., a gold-containing particle), an X-ray dense entity or the like.

According to other preferred embodiments, a secondary and/or a tertiary immunoligand can be used, which is optionally labelled, too.

Preferably, said method is at least one selected from the group consisting of
- ELISA (Enzyme linked Immunosorbent Assay)
- CEDIA (Cloned enzyme donor immunoassay),
- Lateral flow tests (also known as Lateral Flow Immunochromatographic Assays),
- RIA (Radioimmunoassays),
- Immunofluoresence, and/or
- Magnetic immunoassay Performing an ELISA involves at least one antibody or immunoliogand with specificity for a particular antigen. The sample with an unknown amount of antigen is immobilized on a solid support (usually a polystyrene microtiter plate) either non-specifically (via adsorption to the surface) or specifically (via capture by another antibody specific to the same antigen, in a "sandwich" ELISA). After the antigen is immobilized, the detection antibody is added, forming a complex with the antigen. The detection antibody can be covalently linked to an enzyme, or can itself be detected by a secondary antibody that is linked to an enzyme through bioconjugation. Between each step, the plate is typically washed with a mild detergent solution to remove any proteins or antibodies that are aspecifically bound. After the final wash step, the plate is developed by adding an enzymatic substrate to produce a visible signal, which indicates the quantity of antigen in the sample.

In indirect Elisa, a buffered solution of the analyte to be tested for is added to each well of a microtiter plate, where it is given time to adhere to the plastic through charge interactions. A solution of non-reacting protein, such as bovine serum albumin or casein, is added to well (usually 96-well plates) any plastic surface in the well that remains uncoated by the antigen. The primary antibody is added, which binds specifically to the test antigen coating the well. This primary antibody could also be in the serum of a donor to be tested for reactivity towards the antigen. A secondary antibody is added, which will bind the primary antibody. This secondary antibody often has an enzyme attached to it, which has a negligible effect on the binding properties of the antibody. In other cases, as in the diagram to the left, the primary antibody itself is conjugated to the enzyme. A substrate for this enzyme is then added. Often, this substrate changes color upon reaction with the enzyme. The color change shows the secondary antibody has bound to primary antibody, which strongly implies the donor has had an immune reaction to the test antigen. This can be helpful in a clinical setting, and in research. The higher the concentration of the primary antibody present in the serum, the stronger the color change. Often, a spectrometer is used to give quantitative values for color strength. The enzyme acts as an amplifier; even if only few enzyme-linked antibodies remain bound, the enzyme molecules will produce many signal molecules. Within common-sense limitations, the enzyme can go on producing color indefinitely, but the more primary antibody is present in the donor serum, the more secondary antibody+enzyme will bind, and the faster the color will develop.

In sandwich ELISA, a surface is prepared to which a known quantity of capture antibody is bound. Any nonspecific binding sites on the surface are blocked. The antigen-containing sample is applied to the plate. The plate is washed to remove unbound antigen. A specific antibody is added, and binds to antigen (hence the 'sandwich': the Ag is stuck between two antibodies). Enzyme-linked secondary antibodies are applied as detection antibodies that also bind specifically to the antibody's Fc region (nonspecific). The plate is washed to remove the unbound antibody-enzyme conjugates. A chemical is added to be converted by the enzyme into a color or fluorescent or electrochemical signal. The absorbency or fluorescence or electrochemical signal (e.g., current) of the plate wells is measured to determine the presence and quantity of antigen.

A third use of ELISA is through competitive binding. The steps for this ELISA are somewhat different from the first two examples: Unlabeled antibody is incubated in the presence of its antigen (sample). These bound antibody/antigen complexes are then added to an antigen-coated well. The plate is washed, so unbound antibody is removed. (The more antigen in the sample, the less antibody will be able to bind to the antigen in the well, hence "competition".) The secondary antibody, specific to the primary antibody, is added. This second antibody is coupled to the enzyme. A substrate is added, and remaining enzymes elicit a chromogenic or fluorescent signal. The reaction is stopped to prevent eventual saturation of the signal.

Some competitive ELISA kits include enzyme-linked antigen rather than enzyme-linked antibody. The labeled antigen competes for primary antibody binding sites with the sample antigen (unlabeled). The less antigen in the sample, the more labeled antigen is retained in the well and the stronger the signal. Commonly, the antigen is not first positioned in the well.

A new technique called Multiple and portable ELISA uses a solid phase made up of an immunosorbent polystyrene rod with eight to 12 protruding ogives. The entire device is immersed in a test tube containing the collected sample and the following steps (washing, incubation in conjugate and incubation in chromogens) are carried out by dipping the ogives in microwells of standard microplates filled with reagents.

The advantages of this technique are that (i) the ogives can each be sensitized to a different reagent, allowing the simultaneous detection of different antibodies and/or different antigens for multiple-target assays, (ii) the sample volume can be increased to improve the test sensitivity in clinical (blood, saliva, urine), food (bulk milk, pooled eggs) and environmental (water) samples, (iii) one ogive is left unsensitized to measure the nonspecific reactions of the sample and (iv) the use of laboratory supplies for dispensing sample aliquots, washing solution and reagents in microwells is not required, facilitating the development of ready-to-use lab kits and on-site testing.

The enzyme-linked immunosorbent spot (ELISPOT) assay is a common method for monitoring immune responses in humans and other animals. ELISPOT assays were originally developed to enumerate B cells secreting antigen-specific antibodies, and have subsequently been adapted for various tasks, especially the identification and enumeration of cytokine-producing cells at the single cell level. Simply put, at appropriate conditions the ELISPOT assay allows visualization of the secretory product of individual activated or responding cells. Each spot that develops in the assay represents a single reactive cell. Thus, the ELISPOT assay provides both qualitative (type of immune protein) and quantitative (number of responding cells) information.

By virtue of exquisite sensitivity of the ELISPOT assay, frequency analysis of rare cell populations (e.g., antigen-specific responses) which were not possible before are now relatively easy. This exceptional sensitivity is in part because the product is rapidly captured around the secreting cell: before it is either diluted in the supernatant, captured by receptors of adjacent cells, or degraded. This makes ELISPOT assays much more sensitive than conventional ELISA measurements. Limits of detection are below 1/100,000 rendering enumerate the actively producing cells. This allows much of the analysis process to be automated, and permits a greater level of accuracy than what can be achieved using manual inspection.

According to another preferred embodiment, the analyte is detected in a quantitative manner. Preferably, in the method according to the invention at least one carrier molecule is a protein or oligopeptide. Preferably, these carrier molecules have a minimum size of at least 1000 Da, more preferably 5000 Da. Further, these carrier molecules carry functional groups like amino groups and/or carboxylic groups, which make them accessible to binding to small molecular analytes by means of appropriate derivatization.

Preferably, a carrier molecule is used that is inherent to the sample. In this embodiment, naturally occurring carrier molecules are used, e.g., different serum proteins that are part of the sample.

Naturally occurring serum or blood proteins are for example Albumins, Globulins, Fibrinogens, Regulatory proteins or Clotting factors, in particular Prealbuminm Alpha 1 antitrypsin, Alpha 1 acid glycoprotein, Alpha 1 fetoprotein, alpha2-macroglobulin, Gamma globulins, Beta 2 microglobulin, Haptoglobin, Ceruloplasmin, Complement component 3, Complement component 4, Lipoproteins, C-reactive protein (CRP), Lipoproteins (chylomicrons, VLDL, LDL, HDL), Transferrin, Prothrombin, MBL or MBP and naturally occurring mixtures thereof.

Naturally occurring proteins in other body fluids that can act as a sample are, for example,
(i) saliva proteins, like mucopolysaccharides and glycoproteins, α-amylase, lingual lipase, kallikrein, bradykinin, lysozame, lactoperoxidase, lactoferrin, immunoglobulin A, proline-rich proteins
(ii) urine proteins, like bilirubin, albumin, α2u-globulins, immunoglobulins A and M, and other proteins that are associated with proteinuria
(iii) seminal plasma proteins, like prealbumin, albumin, globulin, transferring, α-antitrypsin, β-lipoprotein, β-glycoprotein, orsomucoid, kininogen, peptide hormones, IgG, IgA and IgM According to another preferred embodiment, the at least one carrier molecule is a carrier molecule that is added to the sample.

In this embodiment, a defined carrier molecule can be added to the sample in defined quantities, thus creating standardized conditions. Preferably, prior to adding the carrier molecule to the sample, the sample is deproteinized, in order to remove or at least denaturated all protein which is in the sample, and thus to support the application of standardized conditions.

Deproteinization can be carried out with standard methods known in the art, e.g, by use of tungstic acid, trichloracetic acid (TCA), perchloric acid (PCA) or metaphosphoric acid, followed by neutralization. Other approaches involve a compination of pH adjustment, and heating, or the use of protein adsorption on a column, gel filtration chromatography, as well as a mixture of the aformentioned approaches.

Preferably, the carrier molecule is at least one selected from the group consisting of:
  keyhole limpet hemocyanin (KLH), or modified forms thereof
  Albumins, like bovine serum albumin (BSA), or modified forms thereof
  Blue Carrier* Protein, or modified forms thereof
  Globulins, like Thyroglobulin, or modified forms thereof
  soybean trypsin inhibitor, or modified forms thereof, and/or
  muramyl dipeptide and derivatives, or modified forms thereof.

Most of these carrier molecules are proteins which provide primary amines as substrates for covalent attachment of small molecular analytes (in particular those having a carboxyl group) using a variety of crosslinking techniques (e.g., carbodiimides).

The term "modified forms" alludes to chemically modified variants of the respective carrier, like, e.g., ethylendiamine-modified BSA. The skilled person would readily understand how such concept of modified forms translates to other antigenic carriers. Anyway, the two most commonly used carriers are keyhole limpet hemocyanin (KLH) and bovine serum albumin (BSA).

Keyhole limpet hemocyanin (KLH) is the most widely used carrier protein. The copper-containing polypeptide belongs to a group of non-heme proteins called hemocyanins, which are found in arthropods and mollusks. KLH is isolated from keyhole limpets (*Megathura crenulata*).

Because KLH is from a class of proteins and a group of organisms that are evolutionarily distant from mammals, it is very "foreign" to the mammalian immune system. The protein is also highly immunogenic because of its very large size and complex structure. The molecule is composed of 350 kDa and 390 kDa subunits that associate to form aggregates ranging from 0.5 to 8 million daltons.

Each KLH protein molecule contains several hundred surface lysine groups that provide primary amines as substrates for covalent attachment of small molecular analytes (in particular those having a carboxyl group) using a variety of crosslinking techniques (e.g., carbodiimides). These features make KLH an extremely immunogenic and effective carrier protein for immunogen preparation. Although the large protein is sometimes difficult to work with because it has limited solubility, the commercial availability of stabilized and pre-activated formulations make it convenient to use.

Blue Carrier* Protein is a purified preparation of *Concholepas concholepas* hemocyanin (CCH). The large protein exhibits most of the same immunogenic properties as the popular carrier protein, keyhole limpet hemocyanin (KLH). However, its better solubility provides greater flexibility in immunogen preparation protocols by allowing a broader range of buffer and pH conditions for coupling small molecular analytes using crosslinking methods. The CCH protein is composed of two very large polypeptide subunits (404 and 351 kDa) that form an extremely stable heterodidecameric structure even in the absence of divalent cations. (By contrast, KLH has a less stable and soluble homodidecameric structure). The complex molecular arrangement of CCH subunits contains diverse repeated antigenic structures that elicit a strong immune reaction mediated by T and B lymphocytes.

Because of their large size and molecular complexity, KLH and CCH hemocyanins are carrier proteins of choice for use as immunogens to produce antibodies against small molecular analytes. Moreover, studies suggest that the strong DTH immune response elicited by hemocyanins in animals and in humans may have beneficial therapeutic effects in certain types of cancer. New developments in the immunotherapy of cancer have taken advantage of the unique immunogenic properties of hemocyanins in the development of novel conjugate vaccines for treatment of emerging diseases.

Bovine serum albumin (BSA; 67 kDa) belongs to the class of serum proteins called albumins. Albumins constitute about half the protein content of plasma and are quite stable and soluble. BSA is much smaller than KLH but is nonetheless fully immunogenic. It is a popular carrier protein for weakly antigenic compounds. BSA exists as a single polypeptide with 59 lysine residues, 30 to 35 of which have primary amines as substrates for covalent attachment of small molecular analytes (in particular those having a carboxyl group) using a variety of crosslinking techniques (e.g., carbodiimides).

Cationized bovine serum albumin (cBSA) is prepared by modifying native BSA with excess ethylenediamine, essentially capping all negatively-charged carboxyl groups with positively-charged primary amines. The result is a highly positively-charged protein (pI>11) that has significantly increased immunogenicity compared to native BSA. In addition, the increased number of primary amines provides for a greater number of antigen molecules to be conjugated with typical crosslinking methods.

Another suitable carrier is Ovalbumin (OVA; 45 kDa). Also known as egg albumin, ovalbumin constitutes 75% of protein in hen egg whites. OVA contains 20 lysine groups and is most often used as a secondary (screening) carrier rather than for immunization, although it is somewhat immunogenic. The protein also contains 14 aspartic Acid and 33 glutamic Acid residues that afford carboxyl groups. These groups can be used as targets for conjugation with small molecular analytes. Ovalbumin exists as a single polypeptide chain having many hydrophobic residues and an pI of 4.63. The protein denatures at temperatures above 56° C. or when subject to electric current or vigorous shaking. OVA is unusual among proteins in being soluble in high concentrations of the organic solvent DMSO, enabling conjugation to small molecular analytes that are not easily soluble in aqueous buffers.

Other suitable carriers are bovine thyroglobulin, or soybean trypsin inhibitor. Yet another suitable carrier is Muramyl dipeptide (Acetylmuramyl-Alanyl-Isoglutamine (NAc-Mur-L-ala-D-isoGln), or derivatives thereof, like Murabutide (NAcMur-L-Ala-D-Gln-alpha-n-butyl-ester). Muramyl dipeptide is a peptidoglycan constituent of both Gram positive and Gram negative bacteria. It is composed of N-acetylmuramic Acid linked by its lactic Acid moiety to the N-terminus of an L-alanine D-isoglutamine dipeptide. The immunization of a mammal with complexes of an antigen coupled to muramyl dipeptide enhances the immune response. Other suitable carriers encompass multi-poly (DL-alanine)-poly(L-lysine).

In a preferred embodiment of the method according to the invention the detection immunoligand has been created against an analyte-carrier complex that is identical to the analyte-carrier complex that is being made by derivatization in step a) of the method. This means, e.g., not only in that the analyte and the carrier are the same, respectively, but also in that the crosslinking chemiostry is the same (e.g., use of the same activator, e.g., a carbodiimide-based activator)

It is preferably provided that the detection antibody that specifically binds to the analyte-carrier complex has been created by a method which comprises the following steps:
a) conjugating a small molecular analyte, in isolated form, to a carrier molecule to obtain an immunogenic conjugate,
b) carrying out an immunization experiment with said immunogenic conjugate, and
c) obtaining, directly or indirectly, detection antibodies from said experiment that specifically bind to the analyte-carrier complex and/or to the analyte.

As used herein, the term "carrier molecule" relates to a carrier to which a target molecule is bound in order to induce, in a host, an immune response against the target molecule. Preferably, the carrier is the same as ais being used for derivatization of the anlyte through the detection process. Said carrier may be one that does not elicit an immune response by itself either. However, the conjugate thus produced is immunogenic despite the low molecular weight of the analyte itself. Once the host immunized with the immunogenic conjugate has developed an immune response and generated antibodies against said conjugate, the analyte-carrier complex or the analyte may also be recognized by the produced antibodies.

Such carrier protein can be, principally, any peptide or protein, preferably of a size above 1 kD, that can be coupled with any small molecular analytes. The carrier protein, because it is large and complex, confers immunogenicity to the conjugated small molecular analyte, resulting in production of antibodies against epitopes on the small molecular analyte, and/or the analyte-carrier complex.

To create the best immunogen for this approach, it may be beneficial to prepare the conjugates with several different carriers and with a range of [small molecular analytes]: [carrier] coupling ratios.

Many proteins can be used as carriers and are chosen based on immunogenicity, solubility, and availability of useful functional groups through which conjugation with the small molecular analytes can be achieved.

Further, it is preferably provided that the immunization experiment comprises at least one step selected from the group consisting of:
Immunizing a mammal, obtaining spleen cells from said mammal and fusing them with immortalized cells to obtain antibody-producing hybridoma cells, and/or
Immunizing peripheral blood mononuclear cells which have been obtained from a mammal in vitro.

The first approach is known as the Köhler/Milstein technique, which has for the first time been described in Köhler & Milstein (1975).

This approach works by fusing myeloma cells with spleen cells from a mammal (preferably a mouse) that has been immunized with the above discussed target-carrier construct. Polyethylene glycol can be used to fuse adjacent plasma membranes of both cell types. In order to select hyridoma cells, a selective medium in which only fused cells can grow is used.

This can for example be achieved by exposing cells to aminopterin, which is a folic acid analogue that inhibits dihydrofolate reductase. Myeloma cells have lost the ability to synthesize hypoxanthine-guanine-phosphoribosyl transferase (HGPRT), an enzyme necessary for the salvage synthesis of nucleic acids. However, these cells can tackle the absence of HGPRT unless the de novo purine synthesis pathway is also disrupted. Exposure to aminopterin blocks the de novo pathway and makes myeloma cells fully auxotrophic for nucleic acids requiring supplementation to survive.

Unfused myeloma cells can thus not grow in an aminopterin containing medium, while unfused spleen cells cannot grow indefinitely because of their limited life span. Only fused hybrid cells, referred to as hybridomas, are able to grow indefinitely in such medium, because the spleen cell partner supplies HGPRT and the myeloma partner has traits that make it immortal.

This mixture of hybridoma cells is then diluted, and clones are grown from single parent cells on multi-well plates. The antibodies secreted by the different clones are then assayed for their ability to bind to the antigen with a suitable assay, such as ELISA, Antigen Microarray Assay, or immuno-dot blot. The most productive and stable clone is then selected for future use.

The second approach is also known as "in vitro immunization", and consists, essentially, of immunizing peripheral blood mononuclear cells (PBMC). These can be first treated with 1-leucyl-1-leucine methyl ester (LLME) to remove suppressive cells, and are then immunized with the above discussed target-carrier construct, preferably in the presence of several cytokines and muramyl dipeptide (MDP).

PBMC thus treated can then be transformed with Epstein-Ban virus (EBV), and fused with mouse-human hetero myeloma host cells, to create EBV-immortalized B cell hybridomas.

To efficiently expand antigen-specific B cells in the in vitro-immunized PBMC, cytokines such as IL-2 and IL-4 can be added. Further, CpG oligonucleotides can be used as adjuvants for inducing antigen-specific responses.

An example for such in vitro immunization approach is described in Tamura et al (2007).

In another preferred embodiment, it is provided that the mammal used for immunization, or from which the PMBC have been obtained, is transgenic with respect for at least part of their immunoglobulin gene loci.

This approach encompasses the use of a transgenic mammal (e.g., a rabbit, or a mouse) whose native immunoglobulin gene loci (e.g., Ig-heavy chain and Igκ-light chain loci) have been disrupted and which have transgenes encoding genes for human Immunoglobulin (see, for example, Lonberg et al. (1994). More preferably, the expression of more V gene segments by the transgenic mammal is provided, as described in Lonberg (2005), thereby expanding the potential repertoire of the recovered antibodies.

Transgenic mammal platforms used for such purpose are for example described in US200302048621 by TaconicArtemis.

Antibodies thus obtained are fully human, i.e., they have no non-human sequences at all, and have thus a decreases risk of immunogenicity.

The details of an immunization experiment according to the above embodiment are demonstrated in the examples set forth below.

It can be preferred, in these embodiments, that the binding chemistry to create the immunogenic conjugate as set forth above (consisting of the analyte and the carrier molecule, which conjugate is then used in the immunization experiment to obtain the detection antibody) is the same as the binding chemistry that is actually used for derivatizing the small molecular analyte that is actually in the sample, and which is to be detected. Same applies for the carrier molecule actually used.

This means for example, that, preferably, both (i) in the immunization experiment as well as (ii) prior to the detection of the small molecular analyte an activator is used to crosslink the small molecular analytes to the carrier molecule, namely, e.g., EDC, CMC, DCC, DIC, Woodward's Reagent K, CDI, and/or ECF (see below)

This means further that, preferably, both (i) in the immunization experiment as well as (ii) prior to the detection of the small molecular analyte the same carrier molecule is used, namely, e.g., KLH, BSA, Blue Carrier* Protein, Globulins, like Thyroglobulin, soybean trypsin inhibitor, muramyl dipeptide and derivatives, or modified forms of these carriers (see above).

The latter is particularly preferred in combination with prior deprotonization of the sample as set forth elsewhere herein.

By using the same crosslinking chemistry and the same carrier molecule both (i) in the immunization experiment and (ii) prior to the detection of the small molecular analyte, a high degree of specificity and sensitivity is ensured in the detection method according to the invention, because the detection antibody that is used for detecting a given analyte-carrier-complex has actually been made by immunization with the same analyte-carrier-complex.

In another preferred embodiment, it is provided that the detection immunoligand has been created by a method which comprises the following steps:
a) exposing said analyte, or a analyte-carrier complex to a library of immunoligands, and
b) screening said library for detection immunoligands that specifically bind to the analyte-carrier complex and/or to the analyte.

Libraries of immunoligands are, for example, in vitro antibody libraries. These can be naïve or synthetic libraries, or combinations of both, depending on the source of the antibody repertoire used for the library generation, Naïve libraries are constructed from light and heavy chain repertoires isolated from non-immunised donors. For example, naive libraries consisting of the repertoire of human IgM genes isolated from peripheral blood lymphocytes (PBL) (Marks et al., 1991) and from bone marrow or tonsils (Vaughan et al., 1996) have been constructed.

(Semi-) synthetic libraries can be derived from unrearranged antibody genes of germline cells by cloning the CDR-containing gene segments of the different heavy and light chain families and rearrangement in vitro by PCR (e.g. Hoogenboom and Winter, 1992). Other (semi-) synthetic libraries have "targeted" diversity and consist solely of one or a few VH and VL frameworks and contain partially randomised CDR's. The diversity is introduced by PCRs with DNA-oligonucleotides having degenerated codons at desired positions. Further, in vitro antibody libraries are, among others, disclosed in U.S. Pat. No. 6,300,064 by MorphoSys and U.S. Pat. No. 6,248,516 by MRC/Scripps/Stratagene.

In a preferred embodiment of said method, the exposure and screening process is comprised in an in vitro display method or a high throughput screening method.

The term "in vitro display method" relates to methods in which individual members of an antibody library are displayed on a given entity, while the genetic information encoding said molecule is comprised in said entity. The members of said antibody library are then screened against an immobilized target, and those entities binding the target are then recovered, together with their displaying entity comprising the encoding information, for further analysis. Such methods are reviewed, e.g., in Bradbury et al (2011), and are thus well known to the skilled person.

The term "High-throughput screening" relates to library screening methods using robotics, data processing and control software, liquid handling devices, and sensitive detectors, in order to screen a given library of molecules on an assay plate format, usually based on optical detection. Such methods are, e.g, described by de Wildt et al (2000).

Preferably, the in vitro display method is at least one selected from the group consisting of Phage display
E. coli display
Yeast display
Fungal display
Ribosome display
Retrocyte display These and other techniques are all well known to the skilled person. The following table shows some third party patents related to phage display methods.

| Company | Technology | Alias name | Key IP right US | Key IP right EP |
| --- | --- | --- | --- | --- |
| CAT (now MedImmune) | | Griffiths McCafferty | U.S. Pat. No. 5,885,793 U.S. Pat. No. 5,969,108 | EP0589877 |
| Genentech | Monovalent phage display | | U.S. Pat. No. 5,821,047 | EP0564531 |
| Dyax | | Ladner | U.S. Pat. No. 5,223,409 | EP0436597 |
| Biosite | "Omniclonal" | Dower | U.S. Pat. No. 5,427,908 | EP0527839 |
| Affitech | "MBAS" | Breitling | U.S. Pat. No. 6,387,627 | EP0547201 |
| Crucell | "MAbstract" | | U.S. Pat. No. 6,265,150 | none |
| BioInvent | "Biopanning" | Frendeus | US2006199219 | EP1535069 |
| MorphoSys | "Cys Display" | | U.S. Pat. No. 6,753,136 | EP1144607 |
| Haptogen (now Wyeth) | DNA-binding domain extrusion display ("DBDx") | | U.S. Pat. No. 7,312,074 | EP1009827 |
| Molecular Partners | Cotranslational translocation of fusion polypeptides | Plueckthun | none | EP1902131 |
| Research Development Foundation | IgG expressed in periplasm captured with an Fc-binding fusion protein tethered to inner membrane | Georgiou | WO2008067547 | |

The next table shows some third party patents related to other display methods.

| Company | Technology | Alias name | Key IP right US | Key IP right EP |
| --- | --- | --- | --- | --- |
| Optein (CAT) | Ribosome display | Kawasaki | U.S. Pat. No. 5,643,768 | EP0494955 |
| Univ. Texas | E. coli display | Georgiou | U.S. Pat. No. 5,348,867 | EP0746621 |
| Dade Behring | E. coli display | | | EP0603672 |
| Universiteit Gent | Bacterial display | | U.S. Pat. No. 6,190,662 | EP0848756 |
| Abbott | Yeast display | Wittrup | U.S. Pat. No. 6,300,065 | EP1056883 |
| Novozymes | Fungal display | | U.S. Pat. No. 6,767,701 | EP1124949 |
| Evotec | Beads display | | U.S. Pat. No. 5,849,545 | EP0667960 |
| One Cell Systems | Gel microdroplets (In vitro compartmentalization) | Weaver | U.S. Pat. No. 6,806,058 | EP1399580 |
| Gen Hospital Corp | RNA puromycin | Szostak | U.S. Pat. No. 6,207,446 | EP0971946 |
| Affitech | Cell-based antibody selection ("CBAS") | | none | EP1802980 |
| Res Dev Foundation | Twin arginine translocation (TAT) mediated display | Georgiou | US2003219870 | EP1487966 |
| 4-Antibody | Retrocyte display | | | WO09109368 |

Again, it can be preferred, in these embodiments, that the binding chemistry to create the analyte-carrier complex that is used in the screening method is the same as the binding chemistry that is actually used for derivatizing the small molecular analyte that is actually in the sample, and which is to be detected. Same applies for the carrier molecule actually used.

This means for example, that, preferably, both (i) in the screening method as well as (ii) prior to the detection of the small molecular analyte an activator is used to crosslink the small molecular analytes to the carrier molecule, namely, e.g., EDC, CMC, DCC, DIC, Woodward's Reagent K, CDI, and/or ECF (see below)

This means further that, preferably, both (i) in the screening method as well as (ii) prior to the detection of the small molecular analyte the same carrier molecule is used, namely, e.g., KLH, BSA, Blue Carrier* Protein, Globulins, like Thyroglobulin, soybean trypsin inhibitor, muramyl dipeptide and derivatives, or modified forms of these carriers (see above).

According to a preferred embodiment of the method of the invention, the small molecular analyte to be bound to the carrier comprises at least one carboxyl group.

According to another preferred embodiment of the method of the invention, the small molecular analyte to be bound to the carrier does not comprise, in its native state, a carboxyl group, but undergoes an induced chemical transformation which then creates a carboxyl group. This "induced chemical translation" can either transform an existing functional group into a carboxyl group, or add a molecular entity to the analyte, e.g., by covalent bonding, which molecular entity itself carries such carboxyl group.

In other words: This definition encompasses analytes that have, in their native state, a carboxyl group, as well as those analytes which do not, but which undergo an induced chemical transformation which then creates a carboxyl group. In both cases, however, the carboxyl group then serves as the starting point for derivatization and subsequent coupling to the carrier, e.g., by means of a carbodiimide based coupling agent. See further details below.

Small molecular analytes comprising at least one least one carboxyl group are organic acids, In a preferred embodiment, the small molecular analyte is an endogenous analyte. The term "endogenous analyte", as used herein, shall refer to those analytes which are produced, or used, by the subject body the sample has been derived from, e.g., metabolites and the like.

Figure 2:
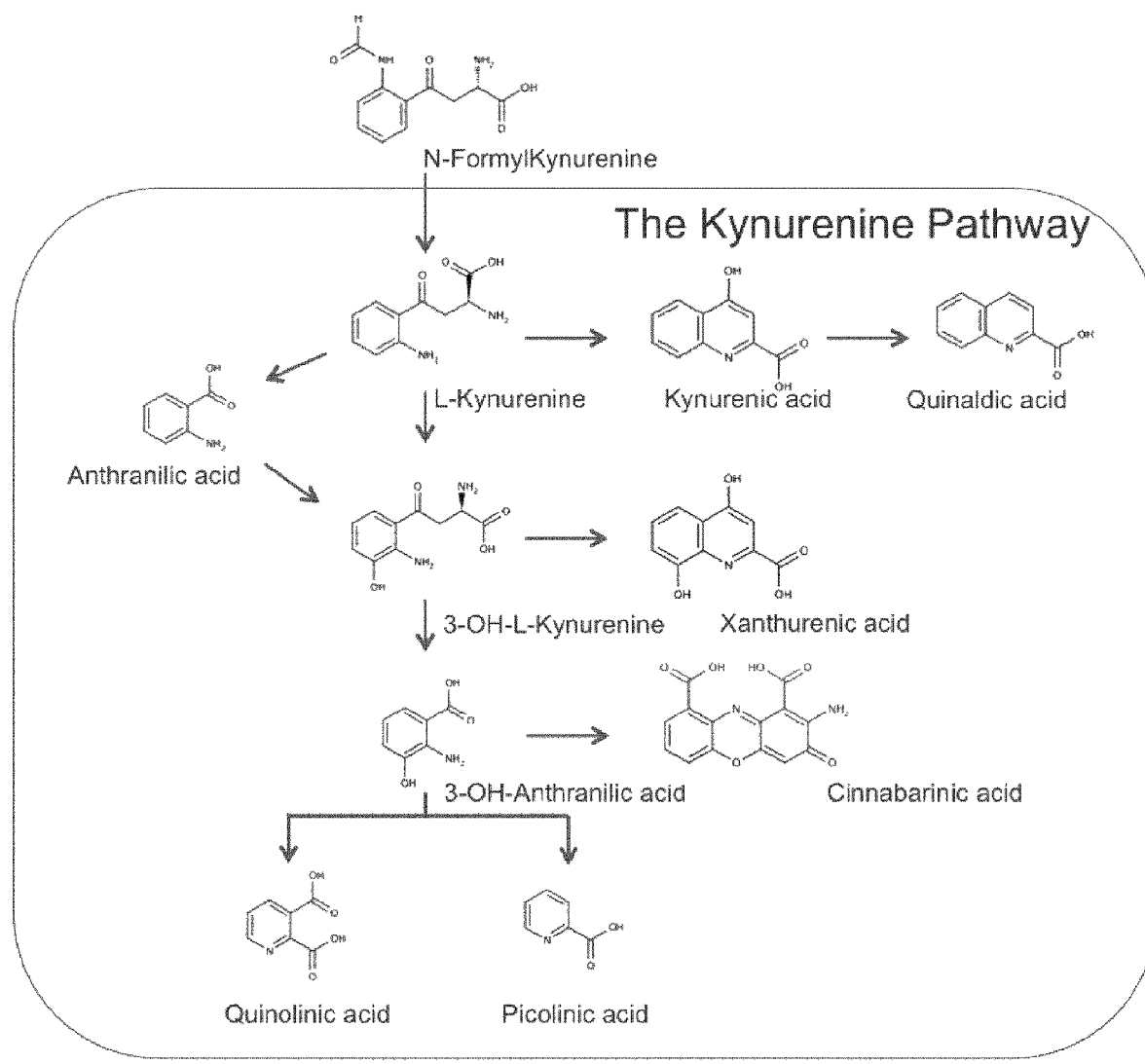

Preferably, but not restrictingly, the endogenous analyte is a metabolite selected from
fatty acid oxidation (α- or β-Oxidation)
Cori cycle
tryptophane pathway
glycolysis or gluconeogenesis
anerobic fermentation (lactic acid pathway, ethanol pathway, propionic acid pathway, botanic acid pathway, formic acid pathway, 2,3-Butandiol pathway, homoacetate pathway, octopin pathway)
citrate cycle/tricarboxylic acid cycle
glyoxylate cycle
oxidative phosphorylation
Q cycle
kynurenine pathway
cholesterol biosynthesis
pentose phosphate pathway
porphyrin synthesis
urea cycle
glutamine metabolism
fatty acid synthesis and -degradation, and/or
amino acid synthesis and -degradation Preferably, the small molecular analyte is a metabolite from the kynurenine pathway, preferably a metabolite selected from the group consisting of
L-Kynurenine
Kynurenic acid
Quinolinic acid
Cinnabarinic Acid,
Xanthurenic Acid,
3-Hydroxyanthranilic acid (3HAA)
Anthranilic acid
Picolinic Acid, and/or
3-Hydroxykynurenine As used herein, the term "kynurenine pathway" encompasses enzymes and metabolites of said pathway). Either of the former two enzymes catalyzes the formation of N-Formylkynurenine (NFK) from Tryptophan. An overview of the kynurenine pathway with its enzymes and metabolites is shown in FIG. 2.

The kynurenine pathway is a metabolic pathway leading to the production of nicotinamide adenine dinucleotide (NAD+) from the degradation of the essential amino acid tryptophan. The kynurenine pathway is involved in physiological functions such as behavior, sleep, thermo-regulation and pregnancy.

There is evidence of kynurenine pathway involvement in neurotoxic mechanisms associated with several inflammatory neurological diseases. Although the pathway is activated in these disorders, kynurenine and its metabolites can play both neurotoxic and neuroprotective roles by influencing neurotransmitter functions and inflammatory pathways peripherally and within the central nervous system.

The inventors have shown that these metabolites seem to be key metabolites can be detected by the techniques according to the invention. These metabolites are part of the Kynurenine pathway. Without being bound to theory, it is assumed that, for example, 3HAA, L-Kynurenine, Quinolinic Acid and/or Cinnabarinic Acid seem to play a key role in the immune escape and tumor growth, blocking of which may thus restore the function of the immune system against the tumor and its oncological properties.

In another preferred embodiment, the small molecular analyte is 2-Hydroxiglutarate.

2-Hydroxyglutarate (2-HG), which has a molecular weight of 148 Da, is a metabolite that is part of different pathways. 2-HG may be formed by mutated isocitrate dehydrogenase (IDH-1 and IDH-2) enzymes, which in unmutated form is part of the tricarboxylic acid cycle (TCA cycle), where they catalyse the conversion of isocitrate to α-ketoglutarate. Mutants of IDH1 and IDH2 found in some cancers convert α-ketoglutarate to 2-Hydroxyglutarate, which has thus been considered as a potential tumor biomarker.

Further, deficiency of D-2-Hydroxyglutarate dehydrogenase, which is a mitochondrial enzyme belonging to the FAD-binding oxidoreductase/transferase type 4 family, and which converts D-2-hydroxyglutarate to 2-ketoglutarate, leads to accumulation of D-2-Hydroxyglutarate. In humans this results in the fatal neurometabolic disorder 2-Hydroxyglutaric aciduria, with symptoms including macrocephaly, cardiomyopathy, mental retardation, hypotonia, and cortical blindness.

At the same time, deficiency of L-2-Hydroxyglutarate dehydrogenase, a FAD-dependent enzyme that oxidizes L-2-Hydroxyglutarate to alpha-ketoglutarate may cause L-2-Hydroxyglutaric aciduria, a rare autosomal recessive neurometabolic disorder resulting in moderate to severe mental retardation, with early symptoms such as hypotonia, tremors, and epilepsy declining into spongiform leukoencephalopathy, muscular choreodystonia, mental retardation, and psychomotor regression.

2-hydroxyglutarate has further been described as a competitive inhibitor of α-ketoglutarate-dependent dioxygenases, and thus having cancer-promoting function. However, 2-hydroxyglutarate has so far not been described to be detectable in Elisa or other immune-based methods yet.

Figure 4:
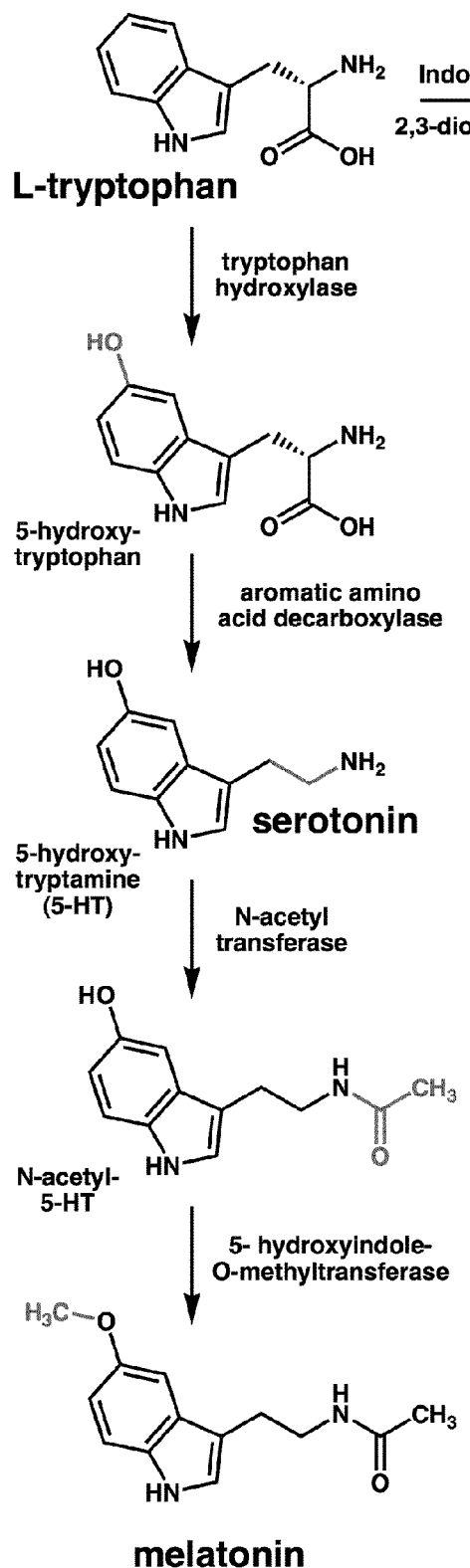

In yet another preferred embodiment, the small molecular analyte is a metabolite from the tryptophane metabolism pathway, preferably a metabolite selected from the group consisting of
L-Tryptophan
Serotonin
Melatonin
5-Hydroxitryptophan, (5HT) and/or
N-acetyl-5-hydroxitryptamin While tryptophane is also the educt for the Knurenine pathway described above (which is, essentially, a tryptophane degradation pathway), the term "tryptophane pathway" describes another metabolism for which tryptophane also acts as an educt, and which results in the formation of melatonin (one arm). Thus, tryptophan functions as a biochemical precursor for, among others, 5-Hydroxytryptophan, Serotonin (which is a neurotransmitter also called 5-Hydroxitryptamine), N-acetyl-5-Hydroxitryptamine and Melatonin (which is a neurohormone). The tryptophane pathway is shown in FIG. 4.

In a preferred embodiment, the small molecular analyte is an exogenous analyte. The term "exogenous analyte", as used herein, shall refer to those analytes which are not produced, or by the subject body the sample has been derived from. This definition includes, for example, environmental compounds that have been taken up by the subject body, like toxins, pollutants and the like, as well as pharmaceutics and the like, essential nutrients (which however can also be considered as endogenous analytes).

According to another preferred embodiment of the method according to the invention, the small molecular analytes are bound to the carrier molecule by means of at least one coupling agent.

Preferably, these coupling agents promote the formation of amide bonds or peptide bonds, preferably bonds in which a carboxylic function of one entity and an amide function of another entity is involved.

In a preferred embodiment of the invention, a carbodiimide coupling agent is used, which is preferably one selected from the group consisting of
1-Ethyl-3-(3-dimethylaminopropyl) Carbodiimide Hydrochloride (EDC)
1-Cyclohexyl-3-(2-morpholinoethyl) carbodiimide (CMC)
N,N'-Dicyclohexylcarbodiimide (DCC)
Diisopropylcarbodiimide (DIC)

Carbodiimides are not traditional crosslinkers in that the crosslinker (i.e., the coupling agent) itself does not become part of the protein-protein complex. Carbodiimides instead covalently link two moieties directly together by forming an amide bond between a carboxylic acid group of one moiety (e.g., the analyte) and an amine group of another (e.g., the carrier protein). Because of the mechanism of carbodiimide crosslinkers, they are by nature zero length, i.e., they do not become part of the molecule, and heterobifunctional crosslinkers.

1-Ethyl-3-(3-dimethylaminopropyl)carbodiimide (EDC) is a water soluble carbodiimide usually obtained as the hydrochloride. It is typically employed in the 4.0-6.0 pH range. It is generally used as a carboxyl activating agent for the coupling of primary amines to yield amide bonds, or to activate corboxyl groups for the coupling to amine groups to yield peptide bonds.

According to another example, 3HAA can be bound to a protein carrier, like BSA, with ethyl chloroformate, which can be used to establish an amide bond between the carboxylic group of 3HAA and a free NH2 group of the protein carrier, e.g., at the N-terminus or at a side chain of lysine residues.

As another example, L-Kynurenine can be activated with the carbodiimide 1-Ethyl-3-(3-dimethylaminopropyl) Carbodiimide Hydrochloride to establish an amide bond between a carboxylic group of L-Kynurenine and a free NH2 group of the protein carrier, e.g., at the N-terminus or at a side chain of lysine residues.

Other approaches are available for conjugating small molecular analytes to antigenic carriers, e.g., carrier proteins. The choice of which conjugation chemistry to use depends on the functional groups available on the small molecular analytes, the required orientation, and the possible effect of conjugation on biological and antigenic properties.

For example, proteins and peptides have primary amines (the N-terminus and the side chain of lysine residues), carboxylic groups (C-terminus or the side chain of aspartic Acid and glutamic Acid), and sulfhydryl groups (side chain of cysteine residues) that can be targeted for conjugation. Preferably, one or more of the many primary amines in a carrier protein are used to couple a small molecular analyte.

Preferably, in the method according to the invention, it is provided that, in case the small molecular analyte to be bound to the carrier comprises, in its native state, an amine group, the method further comprises, prior to the step of derivatizing the analyte, a step of induced chemical transformation of said amine group to obtain a carboxyl group.

Such chemical transformation can for example be effected by use of anhydrides. Anhydrides can acylate amine groups and thus convert the amine functionality to a carboxyl group. For example, succinic, glutaric, maleic or citraconic anhydride can be used for this purpose. Subsequently, the thus-obtained carboxylic group can be used to couple the small molecular analyte to the carrier, and subsequent detection thereof by an immunoligand in the method according to the invention.

Preferably, in the method according to the invention, it is provided that, in case the small molecular analyte to be bound to the carrier comprises, in its native state, a sulfhydryl group, wherein the method further comprises, prior to the step of derivatizing the analyte, a step of induced chemical transformation of said sulfhydryl group to obtain a carboxyl group.

Such chemical transformation can for example be effected by modification with BMPA (N-β-maleimidopropionic acid). The maleimide function of the latter will spontaneously react covalently with the sulfhydryl group, and the rest of the BMPA molecule will then display the carboxylic group that forms part of BMPA. Subsequently, the thus-obtained carboxylic group can be used to couple the small molecular analyte to the carrier, and subsequent detection thereof by an immunoligand in the method according to the invention.

Preferably, in the method according to the invention, it is provided that, in case the small molecular analyte to be bound to the carrier comprises, in its native state, a hydroxyl group, wherein the method further comprises, prior to the step of derivatizing the analyte, a step of induced chemical transformation of said sulfhydryl group to obtain a carboxyl group.

Such chemical transformation can for example be effected by modification with chloroacetic acid. The reaction occurs under basic conditions leading to the formation of an ether bond, and the rest of the chloroacetic acid molecule will then display its carboxylic group. Subsequently, the thus-obtained carboxylic group can be used to couple the small molecular analyte to the carrier, and subsequent detection thereof by an immunoligand in the method according to the invention.

It is evident from these examples that the chemical transformation can encompass both the actual chemical modification of the respective functional group into a carboxylic group, as well as the use of a bifunctional adaptor molecule, part of which binds to the functional group in such way that an carboxylic group of said bifunctional molecule is displayed, and thus available for derivatization and subsequent coupling to the carrier, e.g., by means of the above mentioned carbodiimides.

The above approach provides an efficacious alternative to another preferred embodiment mentioned elsewhere, which provides that the small molecular analyte to be bound to the carriers comprises at least one amine group. This means that, in case of an amide or peptide bound formed, the carrier needs to provide a carboxyl group.

In a preferred embodiment of the method according to the invention, two or more analytes are detected. This embodiment encompasses different sub-embodiments.

In one preferred embodiment (the "multiplex" embodiment), two or more analytes are detected simultaneously in the same sample. This requires that different immunoligands are used which bind to the different analyte-carrier complexes, Preferably, the different detection immunoligands are labelled with different labels (e.g., different fluorophores that have different excitation/emission wavelengths) so that the abundance of the different analytes can be determined individually.

In another preferred embodiment (the "parallel" embodiment), two or more analytes are detected simultaneously in different subsamples. This requires that the sample to be investigated is subdivided into different subsamples, or different aliquots are drawn from the sample, i.e., one subsample or aliquot for each analyte. The subsamples or aliquots are then investigated as described.

The values obtained in the quantification of individual analytes (e.g., Kynurenic acid and Quinolinic acid, or Tryptophane) can be combined for the purpose of disease assessment, e.g., by forming a ratio value of the abundance of these individual analytes. Such ratio analysis, or multiparametric analysis, can provide better information with respect to a given diagnosis, prediction or prognosis. This approach further allows a molecular signature for a given disease, e.g., breast cancer encompass In another preferred embodiment of this approach, the detection of one or more small molecular analytes (e.g., Kynurenic acid) is combined with the detection of one or more protein analytes, e.g., a hormone receptor, to further improve the specificity of a diagnosis, prediction or prognosis.

Further, the use of a method according to the aforementioned claims for the detection of a small molecular analyte in a sample is provided. Preferably, in said method the sample is a patient sample. In another preferred embodiment, said use serves for forensic, scientific, epidemiologic, environmental, predictive, diagnostic or prognostic purposes.

The term Diagnosis, as used herein, means confirmation, or falsification, of given a pathological state or characteristic in a human or animal subject The term "prediction", as used herein, relates to an individual assessment of the malignancy of a disease, e.g., tumor, or to the expected survival rate (DFS, disease free survival) of a patient, if the disease is treated with a given therapy.

The term "prognosis", as used herein, relates to an individual assessment of the malignancy of a disease, e.g., tumor, or to the expected survival rate (DFS, disease free survival) of a patient, if the disease remains untreated.

Definitions

As used herein, the term "immunoligand" shall refer to an

As used herein, the term "detection immunoligand" shall refer to an

As used herein, the term "monoclonal antibody (mAb)" shall refer to an antibody composition having a homogenous antibody population, i.e., a homogeneous population consisting of a whole immunoglobulin, or a fragment or derivative thereof. Particularly preferred, such antibody is selected from the group consisting of IgG, IgD, IgE, IgA and/or IgM, or a fragment or derivative thereof.

As used herein, the term "fragment" shall refer to fragments of such antibody retaining, in some cases, target binding capacities, e.g.
  a CDR (complementarity determining region)
  a hypervariable region,
  a variable domain (Fv)
  an IgG heavy chain (consisting of VH, CH1, hinge, CH2 and CH3 regions)
  an IgG light chain (consisting of VL and CL regions), and/or
  a Fab and/or F(ab)$_2$.

As used herein, the term "derivative" shall refer to protein constructs being structurally different from, but still having some structural relationship to, the common antibody concept, e.g., scFv, Fab and/or F(ab)$_2$, as well as bi-, tri- or higher specific antibody constructs. All these items are explained below.

Methods for the production and/or selection of chimeric, humanised and/or human mAbs are known in the art. For example, U.S. Pat. No. 6,331,415 by Genentech describes the production of chimeric antibodies, while U.S. Pat. No. 6,548,640 by Medical Research Council describes CDR grafting techniques and U.S. Pat. No. 5,859,205 by Celltech describes the production of humanised antibodies. In vitro antibody libraries are, among others, disclosed in U.S. Pat. No. 6,300,064 by MorphoSys and U.S. Pat. No. 6,248,516 by MRC/Scripps/Stratagene. Phage Display techniques are for example disclosed in U.S. Pat. No. 5,223,409 by Dyax. Transgenic mammal platforms are for example described in US200302048621 by TaconicArtemis.

IgG, scFv, Fab and/or F(ab)$_2$ are antibody formats well known to the skilled person. Related enabling techniques are available from the respective textbooks.

As used herein, the term "Fab" relates to an IgG fragment comprising the antigen binding region, said fragment being composed of one constant and one variable domain from each heavy and light chain of the antibody As used herein, the term "F(ab)$_2$" relates to an IgG fragment consisting of two Fab fragments connected to one another by disulfide bonds.

As used herein, the term "scFv" relates to a single-chain variable fragment being a fusion of the variable regions of the heavy and light chains of immunoglobulins, linked together with a short linker, usually serine (S) or glycine (G). This chimeric molecule retains the specificity of the original immunoglobulin, despite removal of the constant regions and the introduction of a linker peptide.

The term "new antibody formats" encompasses, for example bi- or trispecific antibody constructs, Diabodies, Camelid Antibodies, Domain Antibodies, bivalent homodimers with two chains consisting of scFvs, IgAs (two IgG structures joined by a J chain and a secretory component), shark antibodies, antibodies consisting of new world primate framework plus non-new world primate CDR, dimerised constructs comprising CH3+VL+VH, and antibody conjugates (e.g., antibody or fragments or derivatives linked to a toxin, a cytokine, a radioisotope or a label). This list is however not restrictive.

As the inventors of the present invention have shown that L-Kynurenine, 3HAA, Cinnabarinic acid are overabundant in tumor tissue, targeting these metabolites with a specific immunotoxin represents a very promising therapeutic approach of site-directed tumor therapy.

The term "fusion peptide" or "fusion protein" proteins relates, for example, to proteins consisting of an immunoglobulin Fc portion plus a target binding moiety capable of binding an enzyme and/or a metabolite of the kynurenine pathway (so-called-cept molecules).

The term "antibody mimetic" relates to target binding proteins, which are not related to immunoglobulins. Many of the above mentioned techniques, like phage display, are applicable for these molecules as well. Such antibody mimetics are for example derived from Ankyrin Repeat Proteins, C-Type Lectins, A-domain proteins of *Staphylococcus aureus*, Transferrins, Lipocalins, Fibronectins, Kunitz domain protease inhibitors, Ubiquitin, Cysteine knots or knottins, thioredoxin A, and so forth, and are known to the skilled person in the art from the respective literature.

The term "aptamer", as used herein, relates to nucleic Acid species, which are capable of binding to molecular targets such as small molecules, proteins, nucleic Acids, and even cells, tissues and organisms. Aptamers are useful in biotechnological and therapeutic applications as they offer molecular recognition properties that rival that of the commonly used biomolecule, antibodies. In addition to their discriminate recognition, aptamers offer advantages over antibodies or other target binders as they can be engineered completely in a test tube, are readily produced by chemical synthesis, possess desirable storage properties, and elicit little or no immunogenicity in therapeutic applications. Aptamers can for example be produced through repeated rounds of in vitro selection or equivalently, SELEX (systematic evolution of ligands by exponential enrichment) to bind

EXPERIMENTS AND FIGURES

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Example 1: Xanthurenic Acid

Development of a Monoclonal Antibody Targeting Xanthurenic Acid

To build the immunogen, Xanthurenic acid was conjugated to bovine serum albumine (BSA) by means of a carbodiimide crosslinker, which reacts with the carboxylic functions of the targeted molecule and free amine functions of the BSA, to form a stable amide bond. The "Imject BSA and EDC Conjugation Kit" provided by Thermo Scientific is used for this purpose. Others reagents can be used for that purpose.

Monoclonal antibodies are generated following the established method of Köhler and Milstein (1975). Briefly, lymphocytes were isolated from mice immunized three times with the respectives onjugates. These lymphocytes were then fused with murine myeloma cells (SP2O-Ag) with polyethyleneglycol (PEG 1500) to obtain hybridoma cells. The selection of hybridomas cells was realized by enzyme-linked immunosorbent anssay (ELISA). Clones were selected based on their affinity and specificity towards the respective conjugates. In a competitive assay with other metabolites of the Kynurenine pathway, it became evident that the selected antibody has no cross-reactions.

Development of a Novel Immune-Assay for Xanthurenic Acid Quantification in a Sample To mimick a biological fluid (eg. sera), we prepared a solution containing 70 mg/ml of BSA. Solutions containing different amount of Xanthurenic acid was prepared in this buffer. Then, the derivatization process was performed using carbodiimide (EDC) plus N-hydroxysuccinimide (NHS) in MES buffer for 1 hour at 37° C. This final solution was mixed with the selected antibodies and Xanthurenic acid-HRP tracer and was then incubated for 1 h30 on the anti mouse IgG pre-coated plate. Four washes in PBS-T were performed and revelation acetate buffer plus tetratmethyl-benzidine allowed antibodies detection. Optical density (OD) was evaluated at 450 nm. Results were represented by the ratio B/B0 where B0 is the OD obtained with the selected clone and the HRP tracer alone (without L-Kynurenine or L-Tryptophan) and B the OD obtained at a specific concentration.

Example 2: Kynurenic Acid

The Kynurenine pathway produces a neuro-protective metabolite, which is Kynurenic acid, described to be produced during diseases in a lesser extent than normal.

Development of a Monoclonal Antibody Targeting Kynurenic Acid

To build the immunogen, Kynurenic acid was conjugated to bovine serum albumine (BSA) by means of a carbodiimide crosslinker, which reacts with the carboxylic functions of the targeted molecules and free amine functions of the BSA, to form a stable amide bond. The "Imject BSA and EDC Conjugation Kit" provided by Thermo Scientific is used for this purpose. Others reagents can be used for that purpose.

Monoclonal antibodies are generated following the established method of Köhler and Milstein (1975). Briefly, lymphocytes were isolated from mice immunized three times with the respectives onjugates. These lymphocytes were then fused with murine myeloma cells (SP2O-Ag) with polyethyleneglycol (PEG 1500) to obtain hybridoma cells. The selection of hybridomas cells was realized by enzyme-linked immunosorbent anssay (ELISA).

Clones were selected based on their affinity and specificity towards the respective conjugates. In a competitive assay with other metabolites of the Kynurenine pathway, it became evident that the selected antibody has no cross-reactions.

Development of a Novel Immune-Assay for Kynurenic Acid Quantification in a Sample To mimick a biological fluid (e.g., serum), we prepared a solution containing 70 mg/ml of BSA. Solutions containing different amounts of Kynurenic acid as analyte were prepared in this buffer. Then, the derivatization process was performed using carbodiimide (EDC) plus N-hydroxysuccinimide (NHS) in MES buffer for 1 hour at 37° C., to form analyte-carrier conjugates with BSA. This final solution was mixed with the Kynurenic acid antibody and then incubated over night at 4° C. The solution was incubated for 1 h30 min on a Kynurenic acid-BSA conjugate pre-coated ELISA plate and after secondary anti IgG antibody (Abliance) revelation acetate buffer plus tetratmethylbenzidine allowed antibodies detection. Optical density (OD) was evaluated at 450 nm. Results were represented by the ratio B/B0 where B0 is the OD obtained with the selected clone alone (without Kynurenic acid) and B the OD obtained at a specific concentration of Kynurenic acid.

Example 3: Quinolinic Acid

The quinolinic acid is a byproduct of the kynurenine pathway and is thought to be involved in several diseases where it acts as a NMDA receptor agonist resulting in excitatory neurotoxicity. Furthermore, this molecule is described to be elevated in several diseases.

Development of a Monoclonal Antibody Targeting Quinolinic Acid

To build the immunogen, Quinolinic acid was conjugated to bovine serum albumine (BSA) by means of a carbodiimide crosslinker, which reacts with the carboxylic functions of the targeted molecules and free amine functions of the BSA, to form a stable amide bond. The "Imject BSA and EDC Conjugation Kit" provided by Thermo Scientific is used for this purpose. Others reagents can be used for that purpose.

Monoclonal antibodies are generated following the established method of Köhler and Milstein (1975). Briefly, lymphocytes were isolated from mice immunized three times with the respectives onjugates. These lymphocytes were then fused with murine myeloma cells (SP2O-Ag) with polyethyleneglycol (PEG 1500) to obtain hybridoma cells. The selection of hybridomas cells was realized by enzyme-linked immunosorbent anssay (ELISA).

Clones were selected based on their affinity and specificity towards the respective conjugates. In a competitive assay with other metabolites of the Kynurenine pathway, it became evident that the selected antibody has no cross-reactions.

Development of a Novel Immune-Assay for Quinolinic Acid Quantification in a Sample To mimick a biological fluid (e.g., serum), we prepared a solution containing 70 mg/ml of BSA. Solutions containing different amounts of Quinolinic acid as analytes were prepared in this buffer. Then, the derivatization process was performed using carbodiimide (EDC) plus N-hydroxysuccinimide (NHS) in MES buffer for 1 hour at 37° C., to form analyte-carrier conjugates with BSA. This final solution was mixed with the Quinolinic acid antibody and then incubated over night at 4° C. The solution was incubated for 1 h30 min on a Quinolinic acid-BSA conjugate pre-coated ELISA plate and after secondary anti IgG antibody (Abliance) revelation acetate buffer plus tetratmethylbenzidine allowed antibodies detection. Optical density (OD) was evaluated at 450 nm. Results were represented by the ratio B/B0 where B0 is the OD obtained with the selected antibody (without Quinolinic) and B the OD obtained at a specific concentration of Quinolinic acid.

The values obtained in the quantification of individual analytes (e.g., Kynurenic acid and Quinolinic acid) can be combined for the purpose of disease assessment, e.g., by forming a ratio value of the abundance of these individual analytes.

Example 4: Generation of Detection Antibodies

The following section describes the production of detection antibodies against a small molecular target, i.e., the small molecule 3HAA. The inventors have carried out such experiments also to create antibodies against other metabolites of the Kynurenine pathway, in particular against Kynurenic Acid, L-Kynurenine, Xanthurenic acid, Quinolinic Acid and/or Cinnabarinic Acid, as well as against 2 HG and L-Tryptophan, but to avoid repetitions only the production of anti 3HAA antibodies is described in the following. The skilled person will be able to transfer this teaching to other small molecular analytes encompassed by the present invention In an attempt to make antibodies against a small molecular analyte one first needs to prepare the immunogen by crosslinking the small molecule to an immunogenic carrier. The different possibilities to couple a small molecular analyte to a carrier in order to make it immunogenic are discussed herein elsewhere.

In the present experiment, 3HAA was conjugated to bovine serum albumine (BSA) by means of a carbodiimide crosslinker, namely EDC, which reacts with the carboxylic function of 3HAA and free amine functions of the BSA, to form a stable amide bond. The "Imject BSA and EDC Conjugation Kit" provided by Thermo Scientific was used for this purpose.

Production of Monoclonal Antibodies

Monoclonal antibodies were generated following the established method of Köhler and Milstein (Köhler & Milstein 1975). Briefly, lymphocytes were isolated from mice immunized three times with the 3HAA-BSA conjugates. The lymphocytes were then fused with murine myeloma cells (SP2O-Ag) with polyethyleneglycol (PEG 1500) to obtain hybridoma cells. The selection of hybridomas cells was realized by enzyme-linked immunosorbent assay (ELISA).

Clone 5B2-G2 was selected as the most promising clone. Monoclonal antibodies to 3HAA produced by Clone 5B2-G2 had an affinity of $10^{-10}$ M (calculated based on the conjugates amount used to make the competition assay in ELISA, wherein the amount of conjugates is related to amount of BSA). No cross reactions with other metabolites from the kynurenines pathway could be found.

Other Clones

Other hybridooma cell clones developed in the context of the present invention produce monoclonal antibodies against 3HAA, Kynurenine, Cinnabarinic Acid and Quinolinic Acid. These clones are deposited in the laboratory of the inventors.

10 clones have been isolated which produce monoclonal antibodies against 3HAA, 3 clones have been isolated which produce monoclonal antibodies against Kynurenine, 3 clones have been isolated which produce monoclonal antibodies against Cinnabarinic Acid, and 5 clones have been isolated which produce monoclonal antibodies against Quinolinic Acid

| Target | Clone Names |
| --- | --- |
| 3HAA | 6A10-B9, 5G8-D11, 6A1-F2, 6F6-A2,, 4A5-H9, 1A10-D11, 6C4-H9 5B2-G2,, 2A12 |
| Kynurenine | 5C1-G5, 3D4-F2, 2E6-F2 |
| Cinnabarinic Acid | 6D3-A7, 7C7-A2-G9, 5C5-E10 |
| Quinolinic Acid | 1A6-F6, 4E11-G3, 3C10-E5, 1H1-E3, 3B2-C7 |
| Xanthurenic Acid | 6C12-A12 |
| Kynurenic Acid | 4G12-F12 |
| Quinaldic Acid | 5A4-H12 |

Example 4: ELISA Competition Assay

To characterize the monoclonal antibodies, their affinities were evaluated in an ELISA competition assay. Briefly, maxisorp 96 well-plates (Nunc) were coated with the respective conjugated antigen (e.g., 3HAA-BSA for an antibody against the same conjugate) in carbonate buffer (pH=9.6) overnight at 4° C. After saturation with PBS–Tween 0.01%+ BSA 0.25% (ELISA Buffer) for 1 h at 37° C., plates were washed three times with PBS-T (PBS+Tween 0.01%) and antibodies were added. Antibodies were previously incubated with increasing concentration of the respective conjugate or its competitor in ELISA buffer for 1 h30 at 37° C. Three washes in PBS-T were performed and anti mouse IgG (Abliance) were added for 1 hour at 37° C. The solution was then removed, plates washed three times and revelation acetate buffer plus tetratmethylbenzidine allowed antibodies detection. Optical density (OD) was evaluated at 450 nm. Results were represented by the ratio B/B0 where B0 is the OD obtained with the antibodies alone (without any antigen) and B the OD obtained for a specific antigen at a specific concentration. More the antibodies is affine, less conjugate will be necessary to decrease the OD value. For a specific antibody, the ratio B/B0 should not change when the antibodies is incubated with a competitor conjugate.

Example 5: Enzyme Immunoassay (EIA)

Detection of Derivatized Kynurenine by EIA

EIA is different from the classic ELISA since a tracer is used. By tracer we mean the Kynurenine conjugated to Horseradish peroxidase (HRP). Briefly, maxisorp 96 well-plates (Nunc) were coated with anti mouse IgG (Abliance) in carbonate buffer (pH=9.6) overnight at 4° C. After saturation with PBS–Tween 0.01%+BSA 1% (EIA Buffer) for 1 h at 37° C., plates were washed three times with PBS-T and incubated with a mix containing 3D4-F2 antibodies HRP-Kynurenine tracer (0.3 µg/ml) and increasing concentration of Kynurenine derivatized by means of EDC and NHS for 1 hour at 37° C. Four washes in PBS-T were performed and revelation acetate buffer plus tetratmethylbenzidine allowed antibodies detection. Optical density (OD) was evaluated at 450 nm. Results were represented by the ratio B/B0, where B0 is the OD obtained with 3D4-F2 and the Kynurenine-HRP alone (without L-Kynurenine) and B the OD obtained at a specific concentration of L-Kynurenine. The $EC_{50}$ was evaluated at $2*10^{-6}$M.

Detection of Derivatized 3HAA by EIA

Here, by tracer we mean the 3HAA conjugated to Horseradish peroxidase (HRP). Briefly, maxisorp 96 well-plates (Nunc) were coated with anti mouse IgG (Abliance) in carbonate buffer (pH=9.6) overnight at 4° C. After saturation with PBS–Tween 0.01%+BSA 1% (EIA Buffer) for 1 h at 37° C., plates were washed three times with PBS-T and incubated with a mix containing 5B2-G2 antibodies HRP-3HAA tracer (1 µg/ml) and increasing concentration of 3HAA derivatized by means of EDC and NHS for 1 hour at 37° C. Four washes in PBS-T were performed and revelation acetate buffer plus tetratmethylbenzidine allowed antibodies detection. Optical density (OD) was evaluated at 450 nm. Results were represented by the ratio B/B0, where B0 is the OD obtained with 5B2-G2 and the 3HAA-HRP alone (without 3HAA) and B the OD obtained at a specific concentration of 3HAA.

Detection of Derivatized Cinnabarinic Acid by EIA

Here, by tracer we mean the Cinnabarinic Acid conjugated to Horseradish peroxidase (HRP). Briefly, maxisorp 96 well-plates (Nunc) were coated with anti mouse IgG (Abliance) in carbonate buffer (pH=9.6) overnight at 4° C. After saturation with PBS–Tween 0.01%+BSA 1% (EIA Buffer) for 1 h at 37° C., plates were washed three times with PBS-T and incubated with a mix containing 7C7-A2-G9 antibodies, HRP-Cinnabarinic acid tracer (0.03 µg/ml) and increasing concentration of Cinnabarinic acid derivatized by means of EDC and NHS for 1 hour at 37° C. Four washes in PBS-T were performed and revelation acetate buffer plus tetratmethylbenzidine allowed antibodies detection. Optical density (OD) was evaluated at 450 nm. Results were represented by the ratio B/B0, where B0 is the OD obtained with 7C7-A2 and the Cinnabarinic acid-HRP alone (without Cinnabarinic acid) and B the OD obtained at a specific concentration of Cinnabarnic acid. The $EC_{50}$ was evaluated at $1*10^{-8}$M.

Example 6: Production of a Detection Antibody by Means of Phage Display

Methods to produce a human antibody against small molecular target by means of phage display are, e.g., discussed in Brichta et al (2005), Kerrm et al (2003), Keith et al. (2001) or Sheedy et al (2007).

Preparation of Conjugates

3HAA is conjugated to both keyhole limpet haemocyanin (KLH) and bovine serum albumin (BSA) via linkage to 2-mercaptoethylamine, and hapten load/carrier protein is determined to be between eight and 10 haptens per BSA molecule using matrix assisted laser desorption spectrometry. The resulting conjugates are assayed for protein according to standard protocols.

Plasmids and Strains

The Griffin library (MRC Laboratories, Cambridge, UK) consists of the majority of human VH and VL chain gene segments used in vivo, with CDR3 diversity generated using synthetic oligonucleotides (semi-synthetic). The Tomlinson library (MRC Laboratories, Cambridge, UK) is based on a single human framework with side chain diversity (DVT encoded) incorporated at 18 amino Acid positions in the antigen binding site (synthetic). In both libraries, the antibodies are displayed as scFv fragments on the coat protein of filamentous bacteria in the phagemid vector pHEN II. The phagemid clones are maintained and propagated in T-phage resistant E. coli TG1Tr (Stratagene).

Antibody fragments are expressed using the dicistronic, expression vector pIMS147. The vector is inducible with isopropyl L-D-thiogalactosidase (IPTG) and downstream from the scFv genes contains a human CU domain (forming a single chain antibody or scAb) for immunodetection and a hexahistidine tail for purification by nickel chelate affinity chromatography. The antibody expression vector pIMS147 is maintained in *E. coli* strain XL-1 Blue (Stratagene).

Affinity Selection of Antibodies

One hundred microlitres of either Tomlinson or Griffin glycerol stock are inoculated into 100 ml 2×TY broth containing 1% glucose and 100 µg ml$^{-1}$ ampicillin (2×TY-glu-amp), and incubated with shaking at 37° C. to an OD 600 of 0.4. KM13 helper phage ($2\times10^{11}$ pfu) are added to 50 ml of each library culture and the mixture incubated at 37° C. without shaking for 30 min.

Infected cells are pelleted, resuspended in 100 ml 2×TY broth-0.1% glu-amp-50 µg ml$^{-1}$ kanamycin, and incubated overnight with shaking at 30° C. Phage particles are concentrated from each culture supernatant by precipitation with 20 ml polyethylene glycol in 2.5 M NaCl (20% w/v) as described previously.

Two immunotubes are coated overnight with 100 µg ml$^{-1}$ 3 HAA-BSA in phosphate buffered saline (PBS), washed with PBS and blocked with 2% skimmed milk-PBS at room temperature for 2 h. The concentrated phage particles (approximately $1\times10^{13}$) from each library (Griffin or Tomlinson) are added to the immunotubes. Specific scFv phage bound to the antigen, and the unbound phages are removed by washing. The bound scFv phage are eluted from the immunotube with triethylamine (TEA) and infected into exponential phase TG1 cell culture suspension in 2×TY broth for 30 min before being pelleted and plated onto agar plates of TYE-glu-amp and incubated at 30° C. overnight. The colonies are scraped into 5 ml of 2×TY-glu-amp-15% glycerol and stored at –80° C. Fifty microlitres of this stock are used to inoculate 50 ml fresh 2×TY-glu-amp and phage grown, infected and rescued as described above. Selection is repeated a further two times with the following modifications:

pan 2, 3HAA-KLH (100 µg ml$^{-1}$); pan 3, 3HAA-BSA (1 µg ml$^{-1}$).

Screening and Selection of Phage Antibodies

Phage antibody clones (phAbs) that only recognise 3HAA conjugates and not BSA or KLH alone are further characterised using a monoclonal binding ELISA where the phage antibodies are added to the plate in the presence or absence of free 3HAA.

Those phAbs showing reduction of binding compared with phAbs added to the plate alone are sequenced in both directions on an ABI377 automated DNA sequencer (P.E. Applied Biosystems, Foster City, Calif., USA). DNA from clones found to have different H or L chain sequences are digested with NcoI and NotI, and the scFv genes cloned into the similarly digested soluble expression vector pIMS147 before transformation into electrocompetent *E. coli* XL-1 Blue.

Antibodies are then identified which showed binding to 3HAA.

Large Scale Expression and Purification of Anti-Hapten Antibodies

Single *E. coli* XL-1 Blue colonies containing antibodies specific for 3HAA are grown overnight in 5 ml LB containing 1% (w/v) glucose, 50 µg ml$^{-1}$ amp and 12.5 µg ml$^{-1}$ tetracycline at 37° C. using published methods. Each culture is used to inoculate 50 ml Terrific broth (TB)-glu-amp-tet in 250-ml baffled flasks, and the culture is grown to an OD of 15. The cells are pelleted and resuspended in 50 ml fresh TB-amp before induction of antibody expression with IPTG (1 mM final concentration) for 4 h. The cells are pelleted, osmotically shocked and the supernatant containing the periplasmic fraction harvested, ready for purification.

The skilled person will understand that the processes discuses under items 10.1-10.5 can easily be modified in order to produce fully human antibodies against other metabolites of the Kynurenine pathway, like L-Kynurenine, Quinolinic Acid and/or Cinnabarinic Acid.

SHORT DESCRIPTION OF THE FIGURES

FIG. 1: Entry reaction which initiates the kynurenine pathway (L-Tryoptophan→L-Formylkynurenine, but is not part thereof. The step is catalyzed by either a) Indoleamine 2,3-dioxygenase (IDO1) or b) Tryptophan 2,3-dioxygenase (TDO2). If one of the two is blocked, the reaction can still take place, while blocking both may have severe side effects.

FIG. 2: Overview of the kynurenine pathway with its enzymes and metabolites. The enzymes are as follows: i) Kynurenine formamidase, a) Kynurenine amino-transferase, b) Kynurenine 3-hydroxylase (also called Kynurenine mono-oxygenase), c) Kynureninase (also called L-Kynurenine hydrolase), d) Kynurenine amino-transferase, e) Kynureninase (also called L-Kynurenine hydrolase), and f) 3-Hydroxyanthranilic Acid oxygenase (also called 3-Hydroxanthranilate dioxygenase).

The metabolites are as follows: L-Formylkynurenine, Kynuramine, L-Kynurenine, Kynurenic Acid, 3-hydroxyL-kynurenine, Anthranilic Acid, 3-hydroxyanthranilic Acid, Xanthurenic Acid, Quinaldic Acid, Picolinioc Acid and/or Quinolinic Acid.

Please note that some metabolites and enzymes of the kynurenine pathway are not shown. This epplies for example, for Niacin, which is formed out of Quinolinic Acid.

Figure 3:
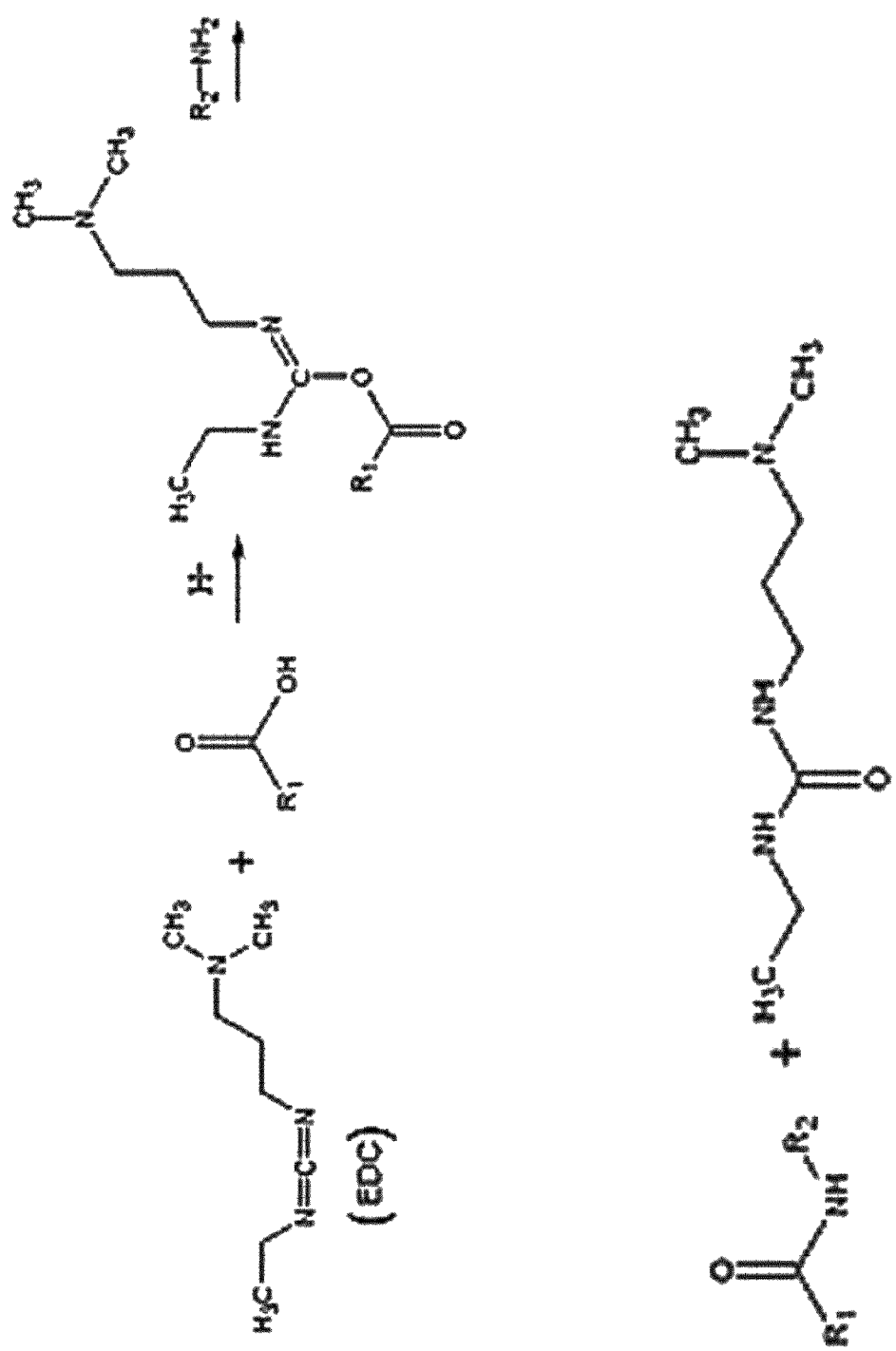

FIG. 3. Crosslinking reaction between a carboxylic acid group of one moiety (R1, e.g., the analyte or the carrier protein) and an amine group of another moiety (R2, e.g., the carrier protein or the analyte), as catalyzed by a carbodiimie. In this case, the latter is EDC (1-Ethyl-3-(3-dimethylaminopropyl)carbodiimide). See more explanations in the text.

FIG. 4 The tryptophan metabolism of L-tryptophan into serotonin and melatonin

Figure 5A:
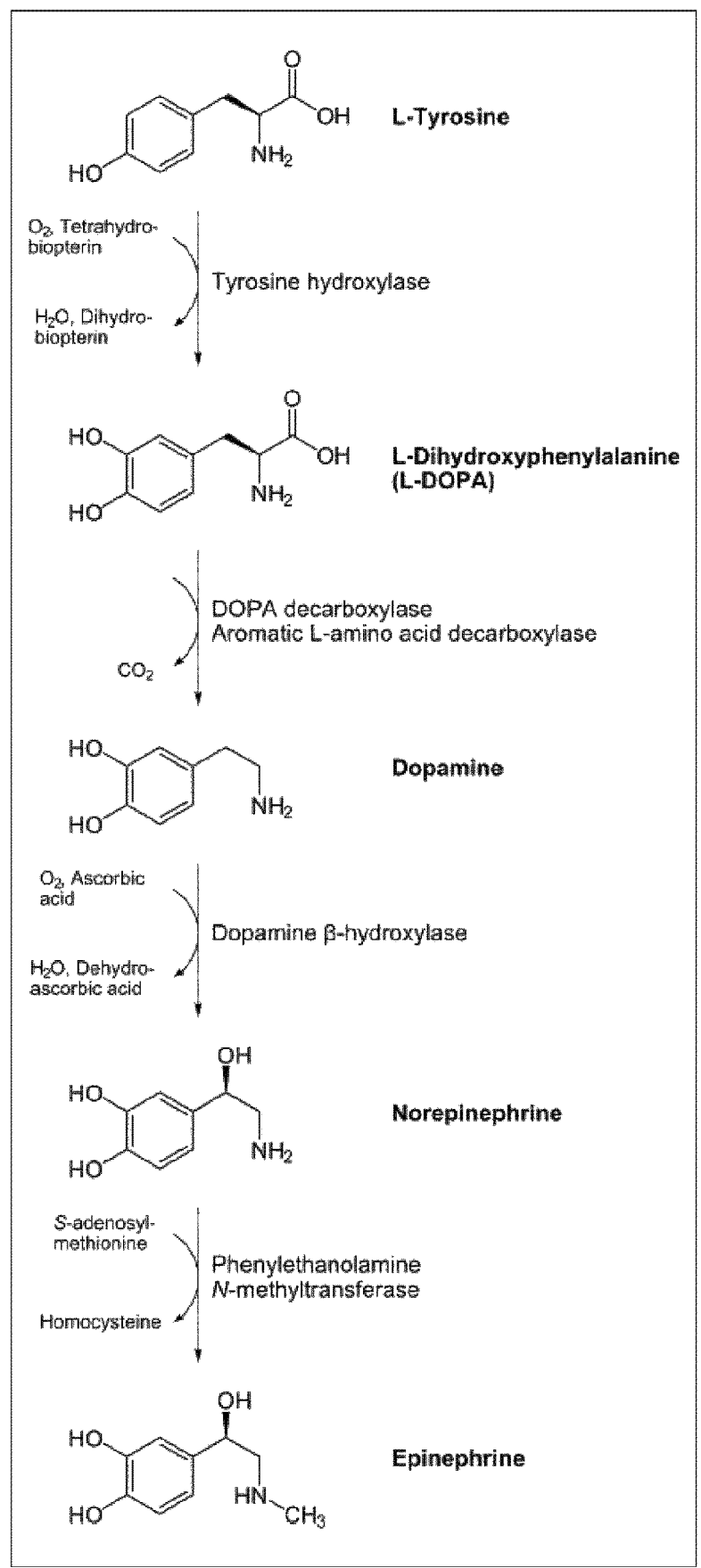

FIG. 5a Tryrosine pathway 1: Conversion of tyrosine to its biologically important derivatives.

Figure 5B:
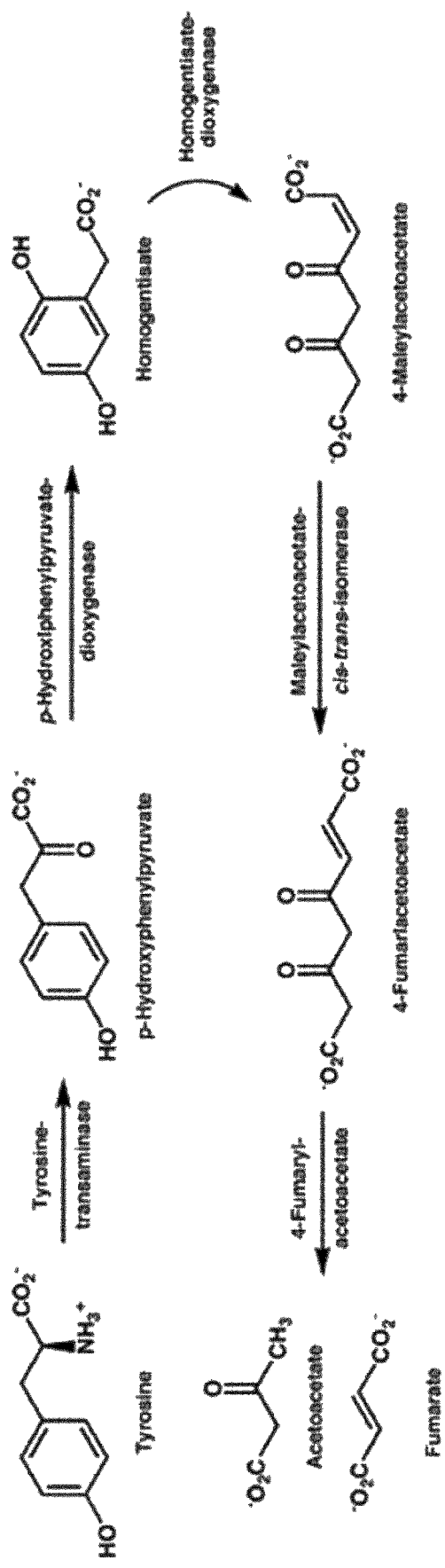

FIG. 5b Tryrosine pathway 2: The decomposition of tyrosine to acetoacetate and fumarate. Two dioxygenases are necessary for the decomposition path. The end products can then enter into the citric acid cycle.

Figure 6:
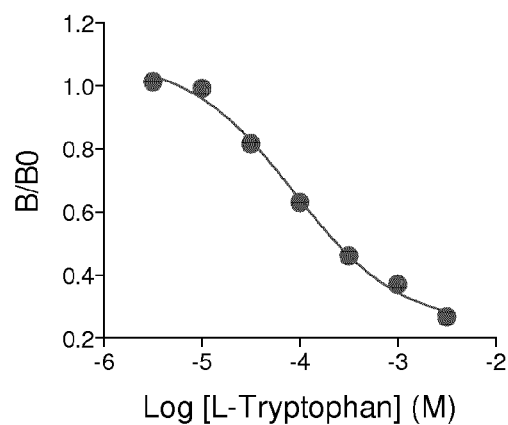

FIG. 6: Detection of L-Tryptophan using competitive ELISA. An increasing concentration of L-Tryptophan was prepared in 70 g/L BSA-supplemented PBS and derivatized using EDC and N-HydroxySuccinimide for 1 hour at 37° C. The product was then incubated with our selected monoclonal antibody over-night at 4° C. The solution was incubated on a maxisporp plate pre-coated with the Tryptophan-BSA conjugate. After HRP-conjugated secondary antibody incubation, the reaction was revealed using TetraMethylBenzidine (TMB). The results are expressed as B/B0, where B0 is the OD (Optical density) value obtained with the antibodies alone while B is the OD value obtained in the presence of a specific concentration of derivatized L-Tryptophan.

Figure 7:
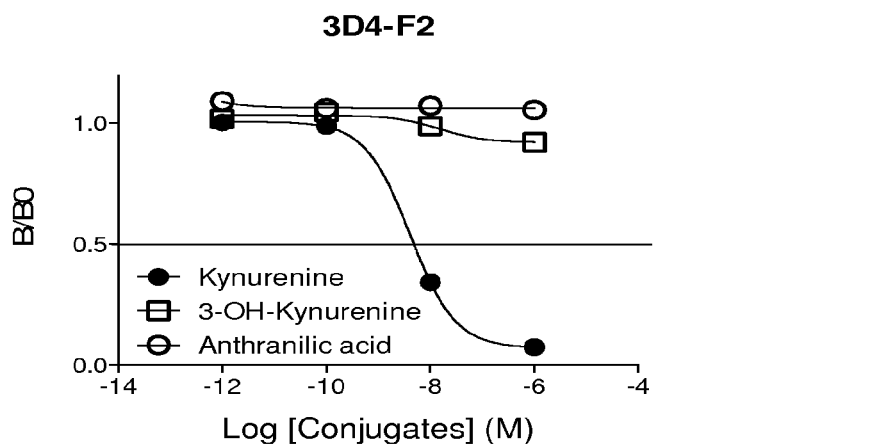
Figure 7:
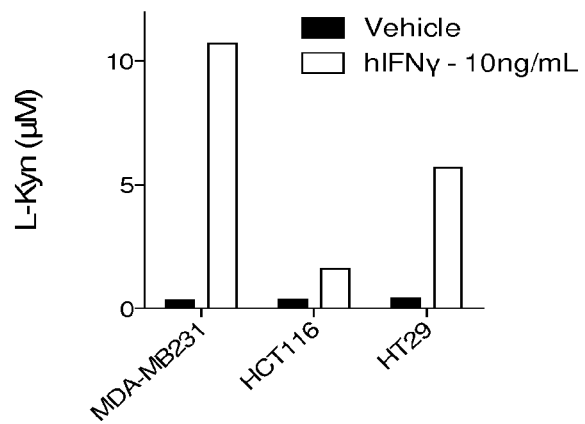
Figure 7:
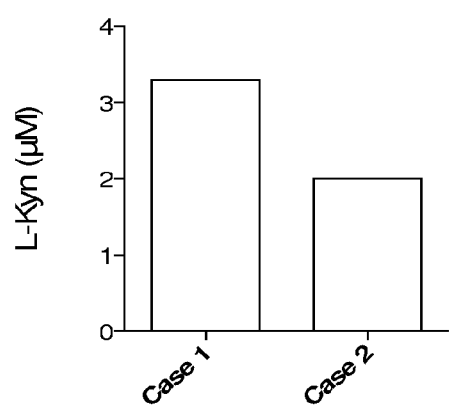
Figure 7:
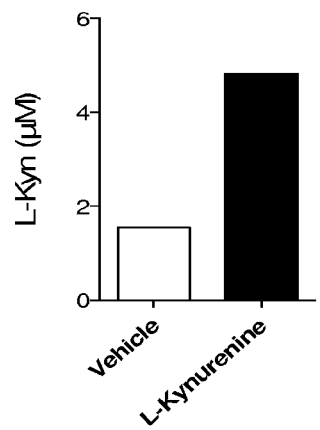

FIG. 7: Detection of L-Kynurenine in a biological fluid using EIA (Enzyme immunoassay).

A) An increasing concentration of Kynurenine-BSA conjugate was incubated with 3D4-F2 mAb (at 0.01 mg/ml) for 1 hour at 37° C. The HRP-Kynurenine conjugate (Tracer) at 1 µg/mL was added and the solution was incubated on a maxisporp plate coated with anti mouse IgG. Reaction was revealed using TetraMethylBenzidine (TMB). The results are expressed as B/B0, where B0 is the OD (Optical density) value obtained with the antibodies (3D4-F2) and the tracer alone while B is the OD value obtained in the presence of a specific concentration of Kynurenine-BSA conjugate.

B) An increasing concentration of L-Kynurenine was prepared in 70 g/L BSA-supplemented PBS and derivatized (L-kynurenine & derivatization) or not (L-kynurenine) using EDC and N-HydroxySuccinimide for 1 hour at 37° C. The solution was incubated with 3D4-F2 monoclonal Antibody (at 0.01 mg/ml) for 1 hour at 37° C. The HRP-Kynurenine conjugate (Tracer) at 1 µg/mL was added and the solution was incubated on a maxisporp plate pre-coated with anti mouse IgG. Reaction was revealed using TetraMethylBenzidine (TMB). The results are expressed as B/B0, where B0 is the OD (Optical density) value obtained with the antibodies (3D4-F2) and the tracer alone while B is the OD value obtained in the presence of a specific concentration of L-kynurenine or derivatized L-Kynurenine.

The same process as described above was used to quantify L-Kynurenine in C) cell culture supernatants from either MDA-MB231, or HCT116, or HT29 stimulated or not with 10 ng/ml of human interferon gamma (hIFNγ) for 24 hours or in D) human urine from two subjects or in E) sera from mice challenged intraperitoneally for 6 hours with either vehicle or 200 mg/kg of L-Kynurenine. For mice sera, a protein precipitation with trichloro acid acetic was performed before the process.

Figure 8:
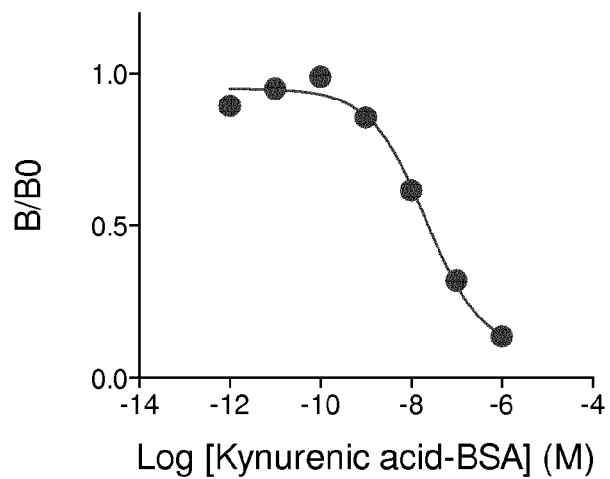
Figure 8:
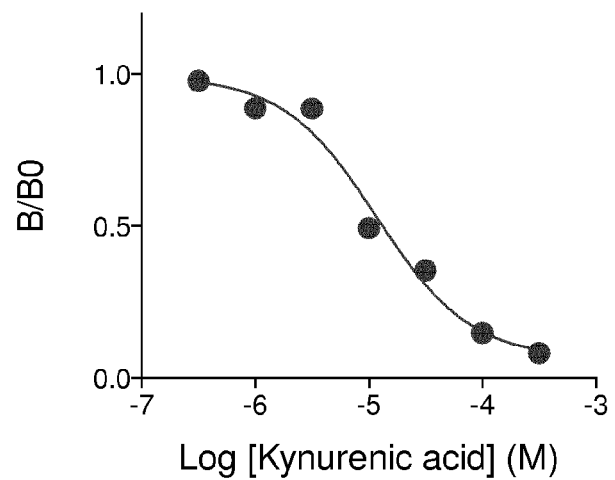

FIG. 8: Detection of Kynurenic acid in a biological fluid using competitive ELISA.

A) An increasing concentration of Kynurenic acid-BSA conjugate was incubated with the selected monoclonal antibody overnight at 4° C. The solution was then incubated on a maxisporp plate coated with Kynurenic acid-BSA conjugate for 1 hour and 30 min at 37° C. After HRP-conjugated secondary antibody incubation, the reaction was revealed using TetraMethylBenzidine (TMB). The results are expressed as B/B0, where B0 is the OD (Optical density) value obtained with the antibodies alone while B is the OD value obtained in the presence of a specific concentration of Kynurenic Acid-BSA conjugate.

B) An increasing concentration of Kynurenic Acid was prepared in 70 g/L BSA-supplemented PBS and derivatized using EDC and N-HydroxySuccinimide for 1 hour at 37° C. The product was then incubated with the selected monoclonal antibody over-night at 4° C. The solution was incubated on a maxisporp plate pre-coated with the Kynurenic acid-BSA conjugate. After HRP-conjugated secondary antibody incubation, the reaction was revealed using TetraMethylBenzidine (TMB). The results are expressed as B/B0, where B0 is the OD (Optical density) value obtained with the antibodies alone while B is the OD value obtained in the presence of a specific concentration of derivatized Kynurenic acid.

Figure 9:
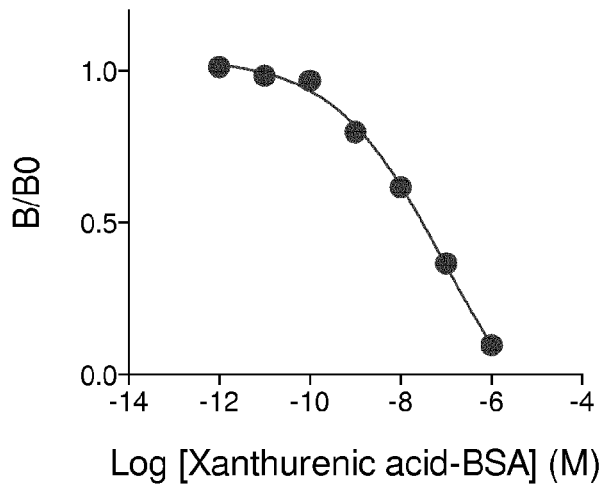
Figure 9:
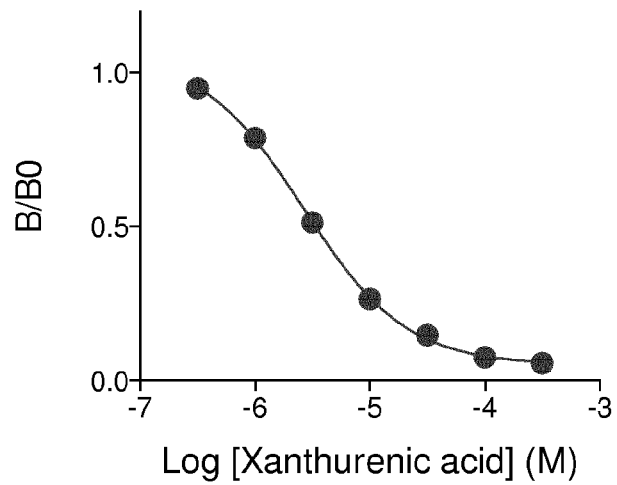

FIG. 9: Detection of Xanthurenic acid in a biological fluid using competitive ELISA.

A) An increasing concentration of Xanthurenic acid-BSA conjugate was incubated with the selected monoclonal antibody overnight at 4° C. The solution was then incubated on a maxisporp plate coated with Xanthurenic acid-BSA conjugate for 1 hour and 30 min at 37° C. After HRP-conjugated secondary antibody incubation, the reaction was revealed using TetraMethylBenzidine (TMB). The results are expressed as B/B0, where B0 is the OD (Optical density) value obtained with the antibodies alone while B is the OD value obtained in the presence of a specific concentration of Xanthurenic Acid-BSA conjugate.

B) An increasing concentration of Xanthurenic Acid was prepared in 70 g/L BSA-supplemented PBS and derivatized using EDC and N-HydroxySuccinimide for 1 hour at 37° C. The product was then incubated with the selected monoclonal antibody over-night at 4° C. The solution was incubated on a maxisporp plate pre-coated with the Xanthurenic acid-BSA conjugate. After HRP-conjugated secondary antibody incubation, the reaction was revealed using TetraMethylBenzidine (TMB). The results are expressed as B/B0, where B0 is the OD (Optical density) value obtained with the antibodies alone while B is the OD value obtained in the presence of a specific concentration of derivatized Xanthurenic acid.

Figure 10:
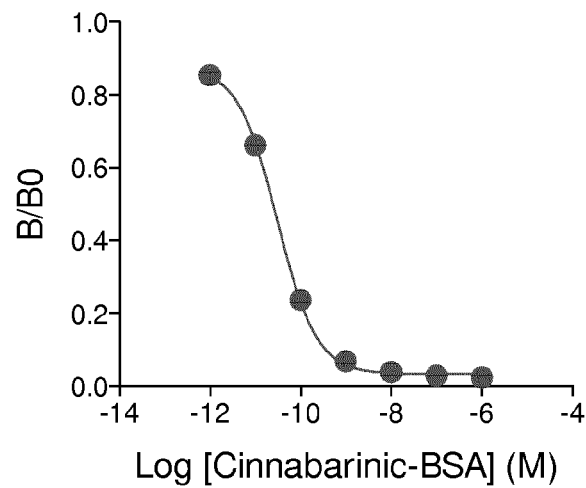
Figure 10:
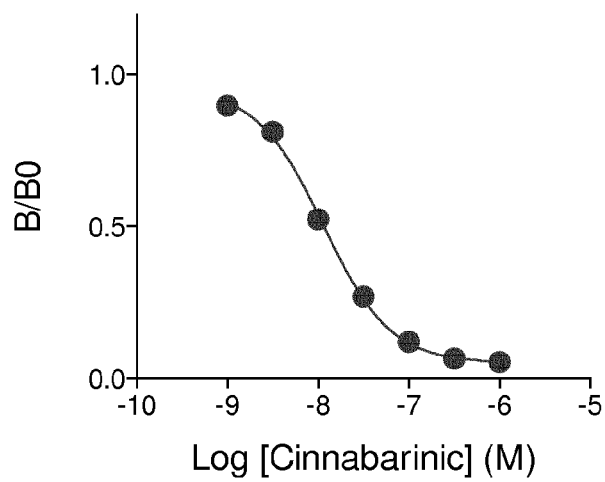

FIG. 10: Detection of Cinnabarinic Acid in a biological fluid using EIA (Enzyme immunoassay).

A) An increasing concentration of Cinnabarinic-BSA conjugate was incubated with 7C7-A2-G9 monoclonal antibody for 1 hour at 37° C. The HRP-Cinnabarinic acid tracer (Tracer) was added and the solution was incubated on a maxisporp plate coated with anti mouse IgG. Reaction was revealed using TetraMethylBenzidine (TMB). The results are expressed as B/B0, where B0 is the OD (Optical density) value obtained with the antibodies (7C7-A2-G9) and the tracer alone while B is the OD value obtained in the presence of a specific concentration of Cinnabarinic acid-BSA conjugate.

Figure 11:
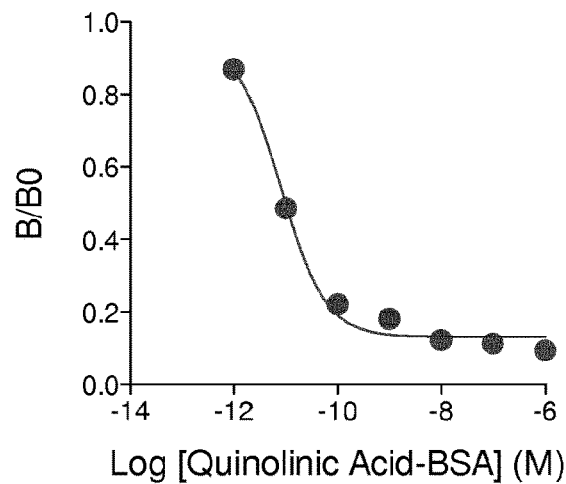
Figure 11:
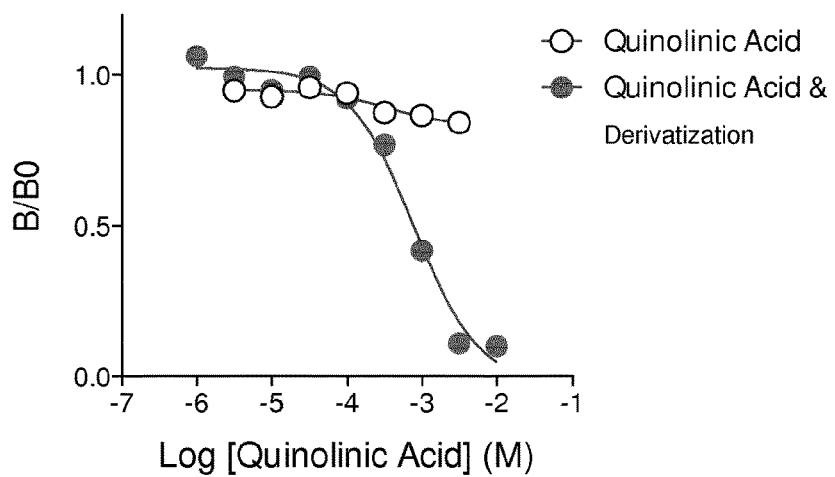

B) An increasing concentration of Cinnabarinic acid was prepared in 70 g/L BSA-supplemented PBS and derivatized using EDC and N-HydroxySuccinimide for 1 hour at 37° C. The solution was incubated with 7C7-A2-G9 monoclonal antibody and the HRP-Cinnabarinic acid tracer (Tracer) before incubation on a maxisporp plate coated with anti mouse IgG. Reaction was revealed using TetraMethylBenzidine (TMB). The results are expressed as B/B0, where B0 is the OD (Optical density) value obtained with the antibodies (7C7-A2-G9) and the tracer alone while B is the OD value obtained in the presence of a specific concentration of Cinnabarinic acid-BSA conjugate FIG. 11: Detection of Quinolinic acid in a biological fluid using competitive ELISA.

A) An increasing concentration of Quinolinic acid-BSA conjugate was incubated with the selected monoclonal antibody overnight at 4° C. The solution was then incubated on a maxisporp plate coated with Quinolinic acid-BSA conjugate for 1 hour and 30 min at 37° C. After HRP-conjugated secondary antibody incubation, the reaction was revealed using TetraMethylBenzidine (TMB). The results are expressed as B/B0, where B0 is the OD (Optical density) value obtained with the antibodies alone while B is the OD value obtained in the presence of a specific concentration of Quinolinic Acid-BSA conjugate.

B) An increasing concentration of Quinolinic acid was prepared in 70 g/L BSA-supplemented PBS and derivatized (Quinolinic Acid & derivatization) or not (Quinolinic Acid) using EDC and N-HydroxySuccinimide for 1 hour at 37° C. The product was then incubated with the selected monoclonal antibody over-night at 4° C. The solution was incubated on a maxisporp plate pre-coated with the Quinolinic acid-BSA conjugate. After HRP-conjugated secondary antibody incubation, the reaction was revealed using TetraMethylBenzidine (TMB). The results are expressed as B/B0, where B0 is the OD (Optical density) value obtained with the antibodies alone while B is the OD value obtained in the presence of a specific concentration of derivatized Quinolinic acid or free Quinolinic acid.

REFERENCES MENTIONED IN THE TEXT

Tamura et al 2007, Biosc Biot Bioch 71 (12): 2871
Lonberg et al. 1994, Nature 368(6474): 856
Lonberg N. Human antibodies from transgenic animals. Nat Biotechnol. 2005 September; 23(9):1117-25.
Bradbury et al, Nat Biotechnol. 2011 March; 29(3): 245-254.
Wildt et al (2000), Nature Biotechnology 18, 989-994
Brichta J, Hnilova M, Viskovic T: Generation of hapten-specific recombinant antibodies:antibody phage display technology: a review. Vet. Med. —Czech, 50, 2005 (6): 231-252
Kerrm Y. F Yaul, Hung Lee, J. Christopher Hall: Emerging trends in the synthesis and improvement of hapten-specific recombinant antibodies. Biotechnology Advances Volume 21, Issue 7, October 2003, Pages 599-637
Charlton Keith A., Porter Andrew J.: Isolation of Anti-Hapten Specific Antibody Fragments from Combinatorial Libraries. Springer Protocols (2001) 178, pp 159-171
Claudia Sheedy, C. Roger MacKenzie, J. Christopher Hall: Isolation and affinity maturation of hapten-specific antibodies. Biotechnology Advances Volume 25, Issue 4, July-August 2007, Pages 333-352
Köhler G, Milstein, C (1975). Continuous cultures of fused cells secreting antibody of predefined specificity". Nature 256 (5517): 495-497.
Marks et al (1991) J. Mol. Biol. 222
Vaughan et al (1996) Nat. Biotechnol. 14, 309-314.
Hoogenboom and Winter (1992) J. Mol. Biol. 227: 381-388.

What is claimed is:

1. An immunoassay method for quantification of small molecular analytes in a liquid sample, wherein the liquid sample comprises one or more carrier proteins, wherein the carrier proteins are inherent to the sample or are added to the sample; and wherein
   (i) the analytes in the liquid sample comprise at least one carboxyl group, or
   (ii) the analytes in the liquid sample are induced to a chemical transformation to provide the analyte having a carboxyl group in the liquid sample;
which method comprises the following steps:
   a) derivatizing the carboxyl group of the analyte according to (i) or (ii) in the liquid sample, by means of at least one coupling agent, in such way that a binding reaction takes place in which the analyte in the liquid sample binds to the carrier proteins in the liquid sample, under the formation of an amide bond in which the carboxylic group is involved thus forming a solution comprising at least one analyte-carrier complex,
   b) adding a detection immunoligand to the solution, wherein the detection immunoligand binds specifically to the analyte-carrier complex, and
   c) detecting after step b), the analyte-carrier complex by a competitive immunoassay;
   wherein the detection immunoligand is a polyclonal or monoclonal antibody, or fragment or derivative thereof, which detection immunoligand has been generated against an analyte-immunogenic carrier complex comprising the analyte conjugated to an immunogenic carrier; wherein the immunogenic carrier is a peptide or protein that confers immunogenicity to the analyte, and wherein the at least one coupling agent is a carbodiimide coupling agent.

2. The method according to claim 1, wherein the immunoligand is labelled.

3. The method according to claim 1, wherein said method is at least one selected from the group consisting of
   ELISA (Enzyme linked Immunosorbent Assay),
   Enzyme Immunoassay (EIA),
   CED IA (Cloned enzyme donor immunoassay),
   Lateral flow tests (also known as Lateral Flow Immunochromatographic Assay),
   RIA (Radioimmunoassay),
   Immunofluoresence, and
   Magnetic immunoassay.

4. The method according to claim 1, wherein the immunogenic carrier is a protein or oligopeptide, preferably selected from the group consisting of:
   keyhole limpet hemocyanin (KLH), or modified forms thereof,
   Albumins, like bovine serum albumin (BSA), or modified forms thereof,
   Blue Carrier™ Protein, or modified forms thereof,
   Globulins, like Thyroglobulin, or modified forms thereof,
   soybean trypsin inhibitor, or modified forms thereof, and
   muramyl dipeptide and derivatives, or modified forms thereof.

5. The method according to claim 1, wherein the detection antibody has been created by a method which comprises the following steps:
   a) conjugating the small molecular analyte, in isolated form, to the immunogenic carrier to obtain an immunogenic conjugate,
   b) carrying out an immunization experiment with said immunogenic conjugate, and
   c) obtaining, directly or indirectly, detection antibodies from said experiment that specifically bind to the analyte-carrier complex and/or to the analyte.

6. The method according to claim 1, wherein the detection immunoligand has been created by a method which comprises the following steps:
   a) exposing said analyte, or said analyte-carrier complex to a library of immunoligands, and
   b) screening said library for detection immunoligands that specifically bind to the analyte-carrier complex and/or to the analyte.

7. The method according to claim 1, wherein the small molecular analyte is an endogenous analyte.

8. The method according to claim 1, wherein the small molecular analyte is
   (i) a metabolite from the kynurenine pathway selected from the group consisting of
      L-Kynurenine,
      Kynurenic acid,
      Quinoline acid,
      Cinnabarinic Acid,
      Xanthurenic Acid,
      3-Hydroxyanthranilic acid (3HAA),
      Anthranilic acid,
      Picolinic Acid, and
      3-Hydroxykynurenine;
   (ii) 2-Hydroxyglutarate; or
   (iii) a metabolite from the tryptophane metabolism pathway selected from the group consisting of
      Tryptophane,
      Serotonin,
      Melatonin,
      5-Hydroxitryptophan, (5HT) and
      N-acetyl-5-hydroxitryptamin.

9. The method according to claim 1, wherein the at least one carbodiimide coupling agent is selected from the group consisting of 1-Ethyl-3-(3-dimethylaminopropyl) Carbodiimide Hydrochloride (EDC)
1-Cyclohexyl-3-(2-morpholinoethyl) carbodiimide (CMC),
N,N'-Dicyclohexylcarbodiimide (DCC), and Diisopropylcarboddimide (DIC).

10. The method according to claim 1, wherein the small molecular analyte to be bound to the carrier comprises, in its native state, an amine group, a sulfhydryl group or a hydroxyl group, wherein the method further comprises, prior to the step of derivatizing the analyte, a step of induced chemical transformation of said amine group, said sulfhydryl group or said hydroxyl group to obtain a carboxyl group.

11. The method according to claim 1, wherein the immunogenic carrier protein that has been used in the analyte-immunogenic carrier conjugate to generate the detection immunoligand is at least one selected from the group consisting of keyhole limpet hemocyanin (KLH), or modified forms thereof, Albumins, like bovine serum albumin (BSA), or modified forms thereof, Blue Carrier* Protein, or modified forms thereof, Globulins, like Thyroglobulin, or modified forms thereof, soybean trypsin inhibitor, or modified forms thereof, and/or muramyl dipeptide and derivatives, or modified forms thereof.

12. The method according to claim 1, wherein the carrier proteins in the sample to which the analyte is conjugated is inherent to the sample.

* * * * *